US009688731B2

(12) United States Patent
Klein et al.

(10) Patent No.: US 9,688,731 B2
(45) Date of Patent: Jun. 27, 2017

(54) **ISOLATION AND APPLICATION OF BAD-1 FOR DIAGNOSING INFECTIONS WITH *BLASTOMYCES DERMATITIDIS***

(71) Applicant: Wisconsin Alumni Research Foundation, Madison, WI (US)

(72) Inventors: Bruce Klein, Madison, WI (US); Theodore Brandhorst, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 87 days.

(21) Appl. No.: 13/720,513

(22) Filed: Dec. 19, 2012

(65) Prior Publication Data

US 2013/0164766 A1 Jun. 27, 2013

Related U.S. Application Data

(60) Provisional application No. 61/579,390, filed on Dec. 22, 2011, provisional application No. 61/579,959, filed on Dec. 23, 2011.

(51) Int. Cl.

| | |
|---|---|
| ***C07K 14/375*** | (2006.01) |
| ***C07K 1/14*** | (2006.01) |
| ***A61K 38/02*** | (2006.01) |
| ***C07K 14/37*** | (2006.01) |
| ***G01N 33/68*** | (2006.01) |
| ***G01N 33/569*** | (2006.01) |

(52) U.S. Cl.
CPC ....... *C07K 14/37* (2013.01); *G01N 33/56961* (2013.01); *G01N 33/6893* (2013.01); *C07K 2319/00* (2013.01); *C07K 2319/02* (2013.01)

(58) Field of Classification Search
CPC ...... C07K 14/37; A61K 39/0002; C12R 1/645
See application file for complete search history.

(56) References Cited

U.S. PATENT DOCUMENTS

| | | | | |
|---|---|---|---|---|
| 5,093,118 | A | 3/1992 | Klein et al. | |
| 5,302,530 | A * | 4/1994 | Klein et al. | 435/320.1 |
| 5,932,102 | A * | 8/1999 | Wyllie et al. | 210/635 |
| 6,248,322 | B1 | 6/2001 | Klein et al. | |
| 7,888,120 | B2 | 2/2011 | Klein et al. | |
| 2010/0316641 | A1* | 12/2010 | Dimitrov | 424/133.1 |
| 2011/0319455 | A1 | 12/2011 | Klein et al. | |

FOREIGN PATENT DOCUMENTS

| | | |
|---|---|---|
| CA | 2342948 | 10/2006 |

OTHER PUBLICATIONS

Audet et al. 1997 (Purification in Quantity of the Secreted Form of WI-1: A Major Adhesion on *Blastomyces dermatitidis* Yeasts; Protein Expression and Purification, Article No. PT970783; vol. 11:219-226).*
Petty 2002 (Metal-Chelate Affinity Chromatography; Unit 10.11 B, Current Portocols in Molecular Biology, Supplement 36: 1-15).*
Reiss et al. 1985 (Characterization of protein and mannan polysaccharide antigens of yeasts, moulds, and actinomycetes. Current topics in medical mycology, (1985) vol. 1, pp. 172-207).*
Nickel Affinity Chromatography Protocol/Guide (DragonTech: A biotechnology service company/Wallert and Provost Lab; published Jan. 2004).*
Zhang et al. 2001 (Role of glucan and surface protein BAD1 in complement activation of *Blastomyce dermatitidis* yeast; Infection and Immunity; 69(12):7559-7564.*
Ueda et al. 2003 (Current and prospective applications of metal ion-protein binding; J Chromatogr A 988:1-23).*
Chaga 2001 (Twenty-five years of immobilized metal ion affinity chromatography: past, present and future; J Biochem Biophys Methods 49:313-334).*
Gaverc-Porekar et al. 2001 (Perspectives of immobilized-metal affinity chromatography; J Biochem Biophys Methods 49: 335-360).*
Audet et al. 1997 (Protein Expression and Purification, Article No. PT970783; vol. 11:219-226).*
Ueda et al. 2003 (J Chromatogr A 988:1-23).*
Chaga 2001 (J Biochem Biophys Methods 49:313-334).*
Reiss et al. 1985 (Current topics in medical mycology, vol. 1, pp. 172-207).*
Bradsher, RW, Chapman, SW, Pappas, PG. Blastomycosis. Infect Dis Clin North Am. 2003;17:21-40.
Brandhorst, et al. Calcium Binding by the Essential Virulence Factor BAD-1 of Blastomyces dermatitidis. J. Biol. Chem. 280(51), 42156-63, 2005.
Newman, S. L., Chaturvedi, S., and Klein, B. S. (1995) J. Immunol. 154, 753-761.
Finkel-Jimenez, B., Wuthrich, M., Brandhorst, T., and Klein, B. S., The WI-1 Adhesin Blocks Phagocyte TNF-α Production, Imparting Pathogenicity on Blastomyces Dermatitidis (2001) J. Immunol. 166, 2665-2673.
Brandhorst, T. T., Finkel-Jimenez, B., Wuthrich, M., Warner, T., and Klein B. S., Exploiting Type 3 Complement Receptor for TNF-a Suppression, Immune Evasion, and Progressive Pulmonary Fungal Infection (2004) J. Immunol. 173, 7444-7453.
Finkel-Jimenez, B., Wuthrich, M., and Klein, B. S., BAD1, an Essential Virulence Factor of Blastomyces dermatitidis, Suppresses Host TNF-α Production Through TGF-β-Dependent and -Independent Mechanisms (2002) J. Immunol. 168, 5746-5755.
Rippon JW. Medical Mycology: The pathogenic fungi and the pathogenic actinomycetes. 3rd ed. Philadelphia, PA: W.B. Saunders; 1988. Blastomycosis; pp. 428-458.

(Continued)

*Primary Examiner* — Gary Nickol
*Assistant Examiner* — Mary Lyons
(74) *Attorney, Agent, or Firm* — Quarles & Brady, LLP

(57) ABSTRACT

Methods for obtaining highly pure native, recombinant or modified BAD-1 protein include the steps of culturing a population of microbes expressing BAD-1 protein in a culture medium, collecting the population of microbes from the culture medium, obtaining a BAD-1 protein-containing solution, and purifying the BAD-1 protein from the solution by combining the BAD-1 protein-containing solution with a nickel-chelating resin, washing the nickel-chelating resin to remove unbound matter, and eluting the BAD-1 protein from the nickel-chelating resin. Highly pure native BAD-1 protein may be used in diagnostic kits for detecting *Blastomyces dermatitidis* infections in animals.

9 Claims, 9 Drawing Sheets

(56) References Cited

OTHER PUBLICATIONS

Mongkolrattanothai K, Peev M, Wheat LJ, Marcinak J. Urine antigen detection of blastomycosis in pediatric patients. Pediatr Infect Dis J. 2006;25:1076-1078.

Hogan et al., Genomic Cloning, Characterization, and Functional Analysis of the Major Surface Adhesin WI-1 on *Blastomyces dermatitidis* Yeasts (1995) J. Biol. Chem. 270, 30725-32.

Brandhorst T, Wuthrich M, Finkel-Jimenez B, Klein B (2003) A C-terminal EGF-like domain governs BAD1 localization to the yeast surface and fungal adherence to phagocytes, but is dispensable in immune modulation and pathogenicity of Blastomyces dermatitidis. Mol Microbiol 48: 53-65.

* cited by examiner

FIG. 6 (SEQ ID NO:1)

```
26199 RAD-1 Sequence- 41 Tandem repeats

MPDIKSVSSILLLVSSSLVAAHPGARYPK-    ← Signal sequence
DDKYPVNVKYSE-
01)   HFHHP KCDW___H_______LWDQWC  ← 1st six repeats degenerate
02)NGDGHKHFYDCGWGLTHPNYNYRLWKYWC        "
03)   DTKVHYNCELDESHLKYDAGLFKSLC        "
04) TGPGKHLYDCDWPTSHVSYSWYLHDYLC        "
05)  GNGHHPYDCELDSSHEDYSWPLWFKWC        "
06) SGHGRHFYDCKWDNDHEKYDWPLWQYWC  ← Start of conserved repeats
07) GSHDKDPYNCDWDKFHEKYDWELWNKWC       1
08)     KDPYNCEWDSSHEKYDWELWNKWC       2
09)     KDPYNCEWNSFHEKYDWELWNKWC       3
10)     KDSYNCEWDSSHEKYDWELWNKWC       4
11)     KDPYNCDWDSSHEKFDWGLWSHWC       } four
12) NDYDKYPYNCEWDSSHKKYDLTLWNRWC       } more
13) SSYDKDPYKCDW__________DLWNQLC      } degenerate
14) SGNGHHFYDCDWDVSYPGYDSHLWDLLC       } repeats
15)    TNNPYNCEWDSSHEKYDWELWDKWC       5
16)     KDPYNCDWDSSHEKYDWDLWNKWC       6
17)     KDPYNCEWDSSHEKYDWELWDKWC       7
18)     KDPYNCDWDSSHEKYDWDLWNKWC       8
19)     KDPYNCEWDSSHEKYDWELWDKWC       9
20)     KDPYNCEWDSSHEKYDWKLWDKWC       10
21)     KDPYNCEWDSSHEKYDWELWDKWC       11
22)     KDSYNCDWDKFHEKYDWELWDKWC       12
23)     KDSYNCDWDKFHEKYDWDLWNKWC       13
24)     KDSYNCDWDKFHEKYDWELWDKWC       14
25)     KDSYNCDWDKFHEKYDWELWDKWC       15
26)     KDPYNCEWDSSHEKYDWELWDKWC       16
27)     KDPYNCEWDSSHEKYDWELWDKWC       17
28)     KDPYNCDWDKFHEKYDWVLWNKWC       18
29)     KDPYNCEWDSSHEKYDWELWDKWC       19
30)     KDPYNCDWDKFHEKYDWDLWNKWC       20
31)     KDPYNCEWDSSHEKYDWELWDKWC       21
32)     KDPYNCEWDSSHEKYDWKLWDKWC       22
33)     KDPYNCEWDSSHEKYDWELWDKWC       23
34)     KDPYNCEWDSSHEKYDWELWDKWC       24
35)     KDPYNCEWDSSHEKYDWELWNKWC       25
36)     KDPYNCEWDSSHEKYDWELWDKWC       26
37)     KDPYNCEWDSSHEKYDWELWDKWC       27
38)     KDPYNCEWDSSHEKYDWELWDKWC       28
39)     KDPYNCEWDSSHEKYDWKLWNKWC       29
40)     KDPYNCEWDSSHEKYDWKLWNKWC       30
41)     KDPYNCEWDSSHEKYDWELWNKWC       31

NKHDEHDKHPWCPVCDPLSGANRCHPTTSCIGTGHSYYCACRAGYKSSHYSHDHKNFRLPPPGYE
FLVFTPPGTECDVLCDGYPHKPAHKLCSEVKVHNYCEP  ← C-term. EGF-like
domain
```

FIG. 7 (SEQ ID NO:2)

14081 BAD-1 Sequence— 22 Tandem repeats

```
MFDTKSVSSILLIVSSSLVAARPCARYPS
DDKYPVDVKYN-
01)    GHPGHPKCDW    H        LWDQWC
02)NGDGHKHFYDCGWGLSDPKYNYDLWSYWC
03)    DTKQHYNCELDESHLKYDAVLWKSSC
04) TGHGKHFYDCDWDPSHGDYSWYLWDYLC
05)  GNGHHPYDCELDNSHEDYNWNLWFKWC
06) SGHGRHFYDCKWDNTHEKYDWLLWQYWC
07) GSNGKDPYNCDWDKSHERYDLNLWNQWC
08)      NKDYYSCEWDSLHEKFNWDLWDHWC
09) NGYDMYPYNCEWDQSHEKYDLTLWNHWC
10) SSYDKDPYKCDWG         LWNGLC
11) SGNGKHFYDCDWDDSHPGYDPHLWDILC
12)      TKDPYNCDWDPSHEKYDWELWNKWC
13)      NKDPYNCDWDPSHEKYDWDLWNKWC
14)       KDPYNCDWDPYHEKYDWDLWNKWC
15)      NKDPYNCDWDPSHEKYDLSLWNKWC
16)       KDPYNCDWDPYHEKYDWDLWNKWC
17)      NKDPYNCDWDPSHEKYDWELWNKWC
18)      NKDPYNCDWDPYHEKYDWDLWNKWC
19)      NKDPYNCDWDPSHEKYDWDLWNKWC
20)      NKDPYNCDWDPYHEKYDWDLWNKWC
21)      NKDPYNCDWDPYHEKYDWDLWNKWC
22)      NKDPYNCDWDPSHEKYDWDLWSKWC
```

NKHDEHDKHPLCPVCDPLSGKNHCHPTTSCVSTGHHYHCACRAGYKASHYSHDHKHFRMPVKGYEFLVFTGPHTKCNVLCDGYP
HKPAHELCGEVKVHNYCGP

N-terminal and C-terminal regions substantially conserved

FIG. 8 (SEQ ID NO: 3)

ER-3 BAD-1 Sequence- 42 tandem repeats

```
MPDIKSVSSILLLVSSSLVAAHPGGARYPR-
DDKYPVNVKYSE-

01)     HFRHPKCDW   H       LWDQWC
02)NGDGHKHFYDCGWGLTHPNYNYRLWKYWC
03)    DTKVHYNCELDESHLKYDAGLFKSLC
04) TGPGKHLYDCDWPTSHVSYSWYLHDYLC
05)  GNGHHPYDCELDSSHEDYSWPLNFKWC
06) SGHGRHFYDCKWDNDHEKYDWPLNQYWC
07) GSHDKDPYNCEWDSSHEKYDWELWNKWC
08)       KDPYNCEWDSSHEKYDWELWNKWC
09)       KDPYNCEWDSSHEKYDWELWNKWC
10)       KDSYNCEWDSSHEKYDWGLWNKWC
11)       KDPYNCEWDSSHEKYDWGLWNKWC
12)       KDPYNCDWDSSHEKFDWGLWSHWC
13) NDYDKYPYNCEWDSSHKEYDLTLWNLWC
14) SSYDKDPYKCDWD         LWNQLC
15) SGNGHHFYDCDWDVSYPGYDSHLWDLLC
16)     TNNPYNCEWDSSHEKYDWDLWNKWC
17)       KDPYNCDWDSSHEKYDWELWDKWC
18)       KDPYNCDWDSSHEKYDWDLWNKWC
19)       KDPYNCEWDSSHEKYDWELWDKWC
20)       KDLYNCEWDSSHEKYDWKLWDKWC
21)       KDSYNCDWDKFHEKYDWELWNKWC
22)       KDPYNCEWDSSHEKYDWELWDKWC
23)       KDPYNCEWDSSHEKYDWELWDKWC
24)       KDPYNCEWDSSHEKYDWELWDKWC
25)       KDSYNCDWDKFHEKYDWELWDKWC
26)       KDSYNCDWDKFHEKYDWDLWNKWC
27)       KDSYNCDWDKFHEKYDWELWDKWC
28)       KDSYNCDWDKFHEKYDWKLWDKWC
29)       KDPYNCEWDSSHEKYDWELWDKWC
30)       KDPYNCEWDSSHEKYDWELWDKWC
31)       KDPYNCDWDKFHEKYDWDLWNKWC
32)       KDPYNCEWDSSHEKYDWELWDKWC
33)       KDPYNCEWDSSHEKYDWELWNKWC
34)       KDPYNCEWDSSHEKYDWELWDKWC
35)       KDPYNCEWDSSHEKYDWELWDKWC
36)       KDPYNCEWDSSHEKYDWKLWDKWC
37)       KDPYNCEWDSSHEKYDWELWDKWC
38)       KDPYNCEWDSSHEKYDWELWDKWC
39)       KDPYNCEWDSSHEKYDWKLWNKWC
40)       KDPYNCEWDSSHEKYDWKLWNKWC
41)       KDPYNCEWDSSHEKYDWKLWNKWC
42)       KDPYNCEWDSSHEKYDWELWNKWC

NKHDEHDKHPWCPVCDPLSGANRCHPTTSCIGTGHSYYCACRAGYKSSHYSHDHKNFRLPPPGYEFLVFT
PPGTECDVLCDGYPHKPAHKLCSEVKVHNYCEP
```

FIG. 9

Known sequence for BAD-1 from 60636 matches 14081 perfectly

```
          DPYHEKYDWDLWNKWC
NKDPYNCDWDPSHEKYDWDLWNKWC
NKDPYNCDWDPYHEKYDWDLWNKWC
NKDPYNCDWDPYHEKYDWDLWNKWC
NKDPYNCDWDPSHEKYDWDLWSKWC

NKHDEHDKHPLCPVCDPLSGKNHCHPTTSCVSTGHHYHCACRAGYKASHYSHDHKHFRMPVKGYEFLVFTGPHTKCNVLCDGYP
HKPAHELCGEVKVHNYCGP
```

FIG. 10 (SEQ ID NO:4)

```
DELTA C-TERM

MKDIKSVEEILLLVSSSLVAAHPGARYTR-      ← Signal sequence
DDKYPVNVKYSE-
01)    HFHHP KCDW___H_______LWDQWC   ← 1st six repeats degenerate
02)NGDGHKHFYDCGWGLTHPNYNYELWKYWC           "
03)    DTKVHYNCELDESHLKYDAGLFKSLC          "
04) TGPGKHLYDCDWPTSHVSYSWYLHDYLC           "
05)  GNGHHPYDCELDSSHEDYSWPLWFKWC           "
06) SGHGRHFYDCKWDNDHEKYDWPLWQYWC     ← Start of conserved repeats
07) GSHDKDPYNCDWDKFHEKYDWELWNKWC           1
08)       KDPYNCEWDSSHEKYDWELWNKWC         2
09)       KDPYNCEWNSFHEKYDWELWNKWC         3
KDSYNCEWDSSHEKYDWELWNKWC                   4
11)       KDPYNCDWDSSHEKFDWGLWSHWC         } four
12) NDYDKYPYNCEWDSSHKKYDLTLWNRWC           } more
13) SSYDKDPYKCDW__________DLWNQLC          } degenerate
14) SGNGHHFYDCDWDVSYPGYDSHLWDLLC           } repeats
15)     TNNPYNCEWDSSHEKYDWELWDKWC          5
16)       KDPYNCDWDSSHEKYDWDLWNKWC         6
17)       KDPYNCEWDSSHEKYDWELWDKWC         7
18)       KDPYNCDWDSSHEKYDWDLWNKWC         8
19)       KDPYNCEWDSSHEKYDWELWDKWC         9
20)       KDPYNCEWDSSHEKYDWKLWDKWC         10
21)       KDPYNCEWDSSHEKYDWELWDKWC         11
22)       KDSYNCDWDKFHEKYDWELWDKWC         12
23)       KDSYNCDWDKFHEKYDWDLWNKWC         13
24)       KDSYNCDWDKFHEKYDWELWDKWC         14
25)       KDSYNCDWDKFHEKYDWELWDKWC         15
26)       KDPYNCEWDSSHEKYDWELWDKWC         16
27)       KDPYNCEWDSSHEKYDWELWDKWC         17
28)       KDPYNCDWDKFHEKYDWVLWNKWC         18
29)       KDPYNCEWDSSHEKYDWELWDKWC         19
30)       KDPYNCDWDKFHEKYDWDLWNKWC         20
31)       KDPYNCEWDSSHEKYDWELWDKWC         21
32)       KDPYNCEWDSSHEKYDWKLWDKWC         22
33)       KDPYNCEWDSSHEKYDWELWDKWC         23
34)       KDPYNCEWDSSHEKYDWELWDKWC         24
35)       KDPYNCEWDSSHEKYDWELWNKWC         25
36)       KDPYNCEWDSSHEKYDWELWDKWC         26
37)       KDPYNCEWDSSHEKYDWELWDKWC         27
38)       KDPYNCEWDSSHEKYDWELWDKWC         28
39)       KDPYNCEWDSSHEKYDWKLWNKWC         29
40)       KDPYNCEWDSSHEKYDWKLWNKWC         30
41)       KDPYNCEWDSSHEKYDWELWNKWC         31

NKHDEHDKHHHHHH ← C-term.
```

FIG. 11 (SEQ ID NO:5)

SEQUENCE TR4

MRGSHHHHHHGIRRRPYNCDWDKSHEKYDWELWDKWCKDPYNCDWDKSHEKYDWELWDK
WCKDPYNCDWDKSHEKYDWELWDKWCKDPYNCDWDKSHEKYDWELWDKWCKDELA

ISOLATION AND APPLICATION OF BAD-1 FOR DIAGNOSING INFECTIONS WITH *BLASTOMYCES DERMATITIDIS*

CROSS REFERENCE TO RELATED APPLICATIONS

This application claims benefit from U.S. Provisional Application 61/579,390, filed Dec. 22, 2011 and U.S. Provisional Application 61/579,959, filed Dec. 23, 2011. These applications are incorporated herein by reference for all purposes.

STATEMENT REGARDING FEDERALLY SPONSORED RESEARCH/DEVELOPMENT

This invention was made with government support under A1035681 awarded by the National Institutes of Health. The government has certain rights in the invention.

BACKGROUND OF THE INVENTION

*Blastomyces dermatitidis* is a fungus found primarily in soil and is endemic throughout the Southeast, Southcentral and Upper Midwestern U.S. and in parts of Canada, India and Africa. Most cases of blastomycosis in the U.S. occur in the Ohio and Mississippi river valleys, the southeastern states, and around the Great Lakes (Bradsher, Chapman, et al., 2003). Blastomycosis typically starts in the lungs after inhalation of conidia or hyphal fragments causing pneumonia-like symptoms and may lead to disseminated disease if not diagnosed and treated early (Brandhorst, et al., 2005). Dogs are particularly vulnerable to infection, especially hunting dogs.

Upon entry into the host, *B. dermatitidis* undergoes a temperature-dependent phase transition into a pathogenic yeast form. Upon transition, yeast phase cells secrete and display on their surface BAD-1 (*Blastomyces* adhesin 1), a 120-kDa multi-functional protein that promotes adherence to macrophages by binding CD11b/CD18 (CR3) and CD14 (Newman, Chaturvedi, et al., 1995) and deviates host pro-inflammatory responses by suppressing tumor necrosis factor-α (TNF-α) (Finkel-Jimenez, Wüthrich, et al., 2001; Brandhorst, Finkel-Jimenez, et al., 2004) and inducing transforming growth factor-β (Finkel-Jiminez, Wüthrich, et al., 2002). Soluble BAD-1 released by wild-type yeast enters macrophages via CR3 receptor-mediated endocytosis, and this event has likewise been demonstrated to suppress tumor necrosis factor-α responses and control of the infection (Finkel-Jiminez, Wüthrich, et al., 2002).

A variety of techniques have been used to aid in the clinical diagnosis of blastomycosis. These include microscopic detection of characteristic broad-based budding yeast forms in body fluids or tissue biopsies, isolation and identification of the organism in culture, detection of *B. dermatitidis*-specific antigens in urine, and detection of specific immunologic responses to infection (Rippon, 1988; Mongkolrattanothai, Peev, et al., 2006). However, clinical tests for blastomycosis suffer from potential false positives due to cross-reactivity with common fungal antigens. One approach to reduce the number of false positives in blastomycosis detection is to use BAD-1, a protein unique to *B. dermatitidis*, as a biomarker for diagnosing blastomycosis infection.

To date, methods for isolating BAD-1 have relied on recombinant BAD-1 proteins, either full length or truncated, that display a 6×His tag and are purified on nickel affinity agarose columns (Finkel-Jimenez, Wüthrich, et al., 2001; Hogan, et al., 1995).

SUMMARY OF THE INVENTION

In one aspect, the present invention relates to a method for the purification of native BAD-1 protein or protein fragments comprising the steps of: a). obtaining a native BAD-1 protein-containing or protein fragment-containing solution; and b). purifying the native BAD-1 protein or protein fragments from the solution by the steps of: i). combining the native BAD-1 protein or protein fragments-containing solution with a suitable divalent cation, ii). washing the suitable divalent cation to remove unbound matter, and iii). eluting the native BAD-1 protein or protein fragments from the nickel-chelating resin.

In another aspect, the present invention relates to a composition comprising highly pure native BAD-1 protein or protein fragments purified from *Blastomyces dermatitidis*, wherein the composition comprises less than about 0.21 mg mannoprotein per mg of native BAD-1 protein or protein fragments.

In another aspect, the present invention relates to a diagnostic method for detecting *Blastomyces dermatitidis* in a mammalian patient suspected of being infected, comprising the steps of: a). providing highly purified native BAD-1 protein or protein fragment, b). preparing a specimen from the mammalian patient and exposing the specimen to the highly purified native BAD-1 protein or protein fragments to form a reaction mixture, and c). analyzing the reaction mixture and determining a diagnosis by using a desired product as the reference, wherein the presence of the desired product in the reaction mixture indicates the mammalian patient is infected with *Blastomyces dermatitidis*.

In another aspect, the present invention relates to a diagnostic kit for detecting an infection of *Blastomyces dermatitidis* in an animal comprising a highly pure native BAD-1 protein or protein fragment.

DESCRIPTION OF THE DRAWINGS

FIG. 6 is the native BAD-1 protein sequence of the 26199 strain (SEQ ID NO:1).

FIG. 7 is the native BAD-1 protein sequence of the 14081 strain (SEQ ID NO:2).

FIG. 8 is the native BAD-1 protein sequence of the ER-3 strain (SEQ ID NO 3).

FIG. 9 shows a domain of the BAD-1 sequence where the known native 60636 strain matches perfectly with the 14081 strain.

FIG. 10 shows the protein sequence of a BAD-1 protein fragment, which is a native BAD-1 protein of the 26199 strain lacking the C-terminus EGF-like domain (Delta C-Term) (SEQ ID NO:4).

FIG. 11 shows the protein sequence of a BAD-1 protein fragment, which includes a four tandem repeat domain set after a six-histidine tag (TR4) (SEQ ID NO:5).

DETAILED DESCRIPTION OF THE INVENTION

Figure 1:
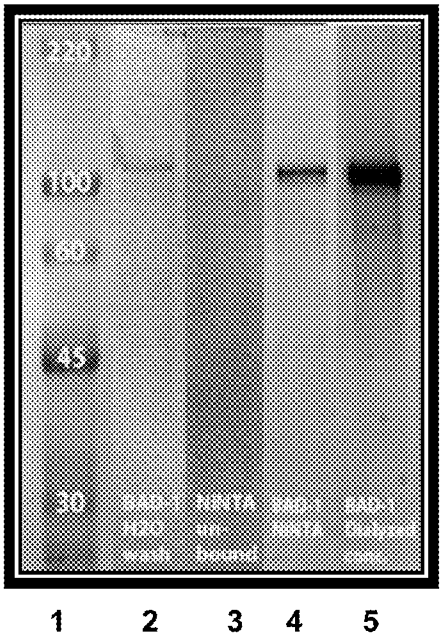
FIG. 1 is a graph of sodium dodecyl sulfate polyacrylamide gel electrophoresis (SDS-PAGE) analysis showing relative protein enrichment by Ni-NTA resin. Coomassie stain of 10% PAGE gel (images collated from 2 separate gels). Lane 1—MW standard (kDa); lane 2—$H_2O$ extract of *B. dermatitidis* yeast; lane 3—protein not bound by Ni-NTA resin; lane 4—Ni-NTA elution fraction; lane 5—BAD-1 after extraction with 10 μg of a conA (concanavalin A)-agarose resin, dialysis against $H_2O$ and concentration via CENTRIPREP® (Millipore, Billerica, Mass.).

A novel method for obtaining large quantities of BAD-1 protein without a 6×His tag or other capture means from batch-cultured microorganisms is described herein. The isolated BAD-1 protein may be native, non-recombinant BAD-1 or a modified recombinant BAD-1, for example, in which the C-terminal epidermal growth factor consensus sequence has been removed. A preferred subsequent purification step may remove contaminating carbohydrates to provide highly pure BAD-1 protein samples for use in diagnostic tests and the like.

As used herein, by use of the term "affinity tag," e.g., a 6×His tag, or other "capture" means, we mean to exclude methods that use cation chelation as a capture mechanism.

As used herein, the phrase "a BAD-1 protein fragment" refers to a fragment or a modified version of wild type BAD-1 that retains at least 90% of the ability to interact with host antibodies of the wild type version of BAD-1. In one embodiment, one may wish to use only selected domains of the native BAD-1 protein, such as Delta C-Term which is a native BAD-1 protein of the 26199 strain lacking the C-terminus EGF-like domain (FIG. 10) and TR4 which includes four tandem repeats domain set after a six-histidine tag (FIG. 11). In another embodiment, one may wish to produce and use a BAD-1 protein or a BAD-1 protein fragment having an affinity or capture tag on the N-terminus or the C-terminus.

Although the purification of the present invention does not require an affinity tag, in one embodiment of the present invention, one may wish to purify the protein via both methods. It was reported that a BAD-1 protein having an affinity tag on the N-terminus or the C-terminus shows a similar activity to that of the native BAD-1 protein (Brandhorst, Wüthrich, et al., 2003). An affinity tag may be a six-histidine tag.

In another embodiment, a BAD-1 protein fragment refers to a modified, preferable conservative alterations, wild type BAD-1 sequence. Typically, a modified or a conservatively altered sequence will comprise 95% sequence identity of the wild type sequence or domain. Modifications may also take the form of deletions and truncations of the wild-type sequence.

As used herein, the term "activity" refers to both the chelating reactivity of the BAD-1 native protein or protein fragments with nickel or other suitable divalent cations and the ability of the BAD-1 native protein or protein fragments to interact with host antibodies. The ability to interact with host antibodies is characteristic of the primary structures of the BAD-1 native protein or protein fragments. Applicants note that the BAD-1 native protein or protein fragments may act as adhesions with related functions to suppress immune response, and the BAD-1 native protein or protein fragments may suppress T cells by ligation of CD47 in a heparin dependent fashion.

In brief, the present invention, as described below and in the figures, is directed to the isolation of BAD-1 protein. For example, highly pure native BAD-1 protein may be obtained using the methodology disclosed herein without the need for developing a recombinant protein, including, for example, a recombinant protein displaying a 6×His tag or other capture means. Consequently, highly pure native BAD-1 isolated using the disclosed method may be obtained more economically for use in diagnostic kits. Moreover, inclusion of highly pure native BAD-1 isolated by the disclosed methodology may be used to achieve greater sensitivity compared to BAD-1 isolated via other means.

In one embodiment, the present invention is the isolation of native BAD-1 protein or a BAD-1 protein fragment by nickel chelation without the addition of a histidine tag or other capture means added to the protein or protein fragment. In other embodiments, one may substitute nickel with other divalent cations such as manganese, copper, zinc, and others, which show similar affinity with the native protein or the protein fragment to nickel. We refer to these cations as "suitable divalent cations".

To obtain a native protein, in one preferred embodiment, one would first obtain a cell culture, preferably *Blastomyces dermatitidis* strain 26199 (ATCC). In other embodiments, one may use other strains of *Blastomyces dermatitidis* suitable for the present invention. A suitable strain would be any of the various isolates that produces and secretes BAD-1. Applicants note that there are strains that do not produce BAD-1, such as African isolates. Clinical isolates may be preferred, as BAD-1 is a virulence factor, but any BAD-1 producing strain should suffice. For example, native 14081 strain and ER-3 strain are suitable for the present invention (FIG. 7 and FIG. 8).

The Examples below describe a typical culture preparation. The Examples below also describe the preparation of a typical "BAD-1 protein-containing solution." One may obtain a BAD-1 protein-containing solution by exposing yeast to a low osmotic, divalent cation-free buffer (for example, distilled water [$dH_2O$]). The BAD-1 containing solution is extracted in this solvent and centrifuged, followed by filter sterilization to remove yeast.

The BAD-1 containing solution is adjusted in pH and salinity, preferably by adding phosphate buffer, pH8 to a final concentration of 20 mM, and NaCl to a final concentration of 300 mM. One then exposes the BAD-1-containing solution to a nickel-chelating resin (for example, Ni-NTA). The Examples below disclose a ratio of 10 ml of Ni-NTA for every liter of original yeast volume. However, this ratio may be modified depending on desired yield of BAD-1 and the amount of starting materials. An optimal ratio of resin to BAD-1 protein or protein fragment may be determined empirically for any given BAD-1 protein or protein fragment isolate. Typically, the ratio may fall within the range between 1 ml of resin for every 10 mg BAD-1 protein or protein fragment to be isolated and 10 mls of resin for every 1 mg of BAD-1 protein or protein fragment to be isolated.

The Examples below disclose the combination of the Ni-NTA resin and the buffer extract containing BAD-1, preferably mixing with agitation for one hour at 4° C. The resin is preferably packed into a column and the columns are washed with buffer, preferably, 10 volumes of 20 mM phosphate buffer containing 300 mM NaCl at a temperature of 4° C. Without wishing to be bound by theory, it is believed that the higher pH and higher salinity of the preferred wash buffer may lead to more optimal purifications, compared to traditionally formulated PBS. For example, a PBS buffer with a pH of 8 and containing 300 mM NaCl is contemplated as an alternative buffer. The examples below disclose elution of the protein with 250 mM imidazole in PBS buffer at 4° C. As alternatives to an imidazole-containing buffer, it is contemplated that either a histidine-containing buffer or a buffer with a low pH may serve to elute BAD-1 from nickel-chelating resin.

Preferably, one would also wish to extract the mannoproteins from the solution. The Examples below describe a preferred extraction using concanavalin-agarose resin. However, any technique that might reduce and/or remove mannan is contemplated herein. For example, other techniques that may be used to purify BAD-1 from solution in order to minimize mannan and other contaminants include, for example, those that separate proteins based on anion exchange, saline gradients, size exclusion, hydrophobic interactions, and the like.

Preferably, imidazole is then removed from the collected eluate and the samples are dialyzed and concentrated. One may easily achieve protein concentrations at or above about 4 mg/ml, or about 1 mg/ml, or about 2 mg/ml, or about 3 mg/ml, or from about 1 mg/ml to about 4 mg/ml. In one embodiment, one may easily achieve protein concentrations at or above about 4 mg/ml, up to 12 mg/ml.

By "highly purified BAD-1 protein," a preparation of BAD-1 protein that preferably comprises less than about 0.21 mg mannoprotein and at least about 1 mg BAD-1 protein per milliliter solution is meant. This concentration of mannoprotein is measured prior to extraction of the BAD-1 protein preparation with concanavalin-agarose resin. After extraction, the concentration of mannoprotein in the BAD-1 protein preparation is typically reduced to about 0.15 mg/ml. BAD-1 protein concentration in the preparation remains substantially unaffected by concanavalin-agarose resin extraction of mannoproteins. Preferably, BAD-1 protein concentration is at least about 1 mg/ml. These amounts may be achieved from a 1 liter culture of yeast.

We note that the same general methods can be used for purifying recombinant BAD-1 protein, modified BAD-1 protein or recombinant protein fragments without the addition of a histidine tag or any other capture means according to methods described above. The preparation of the present invention is especially useful for clinical diagnostic tests. The present invention is a simplified method of obtaining sufficient amounts of native BAD-1 proteins for testing.

Though both 6×His tagged and native BAD-1 proteins may be purified by nickel chelation, one advantage recognized by the present disclosure is that production of the recombinant form from yeast strains harboring the altered protein can be somewhat unstable, and these strains must be maintained in an antibiotic-containing medium (for example, chlorimuron ethyl). Even under such selection conditions, recombinant protein production levels can fall over time. This is less of a problem when working with native strains, as the present disclosure allows.

In another embodiment, the present invention is directed to a highly purified native BAD-1 protein or BAD-1 protein fragments. As disclosed in Brandhorst, Gauthier, et al., a native BAD-1 protein has three domains: 1) an N-terminus that harbors a secretion signal governing its trafficking; 2) a core domain of 25 amino acids arrayed in tandem in 30 to 40 copies, representing a so-called "tandem repeat region"; and 3) a C-terminus harboring an epidermal growth factor (EGF)-like consensus sequence.

In a preferred embodiment, the present invention relates to a highly purified native BAD-1 protein. FIGS. 6-8 depict the protein sequence of native BAD-1 proteins, obtained from ATCC wild-type strain 26199, 14081, and ER-3, respectively. Specifically, as shown in FIG. 6, the protein sequence of the 26199 native BAD-1 protein (SEQ ID NO:1) includes an N-terminal signal sequence of MPDIKSVSSILLLVSSSLVAAHPGARYPR, a 41 tandem repeat domain, and a C-terminal, EGF-like domain. As shown in FIG. 7, the protein sequence of the 14081 native BAD-1 protein (SEQ ID NO:2) includes an N-terminal signal sequence of MPDIKSVSSILLLVSSSLVAARPGARYPR, a 22 tandem repeat domain, and a C-terminal, EGF-like domain. As shown in FIG. 8, the protein sequence of the ER-3 native BAD-1 protein (SEQ ID NO:3) includes an N-terminal signal sequence of MPDIKSVSSILLLVSSSLVAAHPGGARYPR, a 42 tandem repeat domain, and a C-terminal, EGF-like domain. A comparison between these native BAD-1 protein sequences demonstrates that N-terminal and C-terminal regions are substantially conserved. Further, FIG. 9 shows that the domain of the known sequence for BAD-1 from the strain 60636 matches perfectly with that from the strain 14081.

A method to produce native BAD-1 proteins is well know in the art (e.g., Brandhorst, Wüthrich, et al., 2003; Brandhorst, Gauthier, et al., 2005), and a highly purified native BAD-1 protein may be obtained after the as-prepared native BAD-1 protein is purified using the protocol as discussed above.

In other embodiments, one may wish to obtain a highly purified native BAD-1 protein having a six-histidine affinity tag at the end of the C-terminal EGF-like domain. A highly purified native BAD-1 protein having a six-histidine tag at the end of C-terminus may be initially produced using a previous reported protocol (Brandhorst, Wüthrich, et al., 2003), and consequently following a purification process as discussed above.

In one embodiment, the present invention is directed to highly purified BAD-1 protein fragments. The highly purified BAD-1 protein fragments may include a native BAD-1 protein, e.g., those in FIGS. 6-8, lacking at least one part of each domain of the N-terminal signal sequence, the tandem repeat domain, and the C-terminal EGF-like domain. For instance, a BAD-1 protein fragment may be a native BAD-1 protein lacking a C-terminal EFG-like domain. A BAD-1 protein fragment may also be a native BAD-1 protein lacking part or complete domain of the tandem repeat domain. A BAD-1 protein fragment may also be a native BAD-1 protein lacking both part or complete domain of the tandem repeat domain and the C-terminal EGF-like domain. In other embodiments, one may wish to obtain a highly purified BAD-1 protein fragment, having a six-histidine affinity tag either at the beginning of the N-terminal signal sequence or at the end of the C-terminal EGF-like domain. BAD-1 protein fragments may be produced following methods reported in Brandhorst, Wüthrich, et al., 2003 or in Brandhorst, Gauthier, et al., 2005, and a highly purified BAD-1 protein fragment may be obtained after the as-prepared native BAD-1 protein is purified using the protocol as discussed above.

FIG. 10 shows one example of the BAD-1 protein fragment named Delta C-term. Delta C-term (SEQ ID NO:4) is a native BAD-1 protein of the 26199 strain lacking a C-terminal EGF-like domain. Essentially, Delta C-term replaces the last 95 amino acids of the native BAD-1 protein of the 26199 strain with a six-histidine tag.

FIG. 11 shows another example of the BAD-1 protein fragment denoted TR4 (SEQ ID NO:5). TR4 includes four tandem repeat set after a six-histidine tag.

In one embodiment, the present invention is directed to a diagnostic method using the highly purified BAD-1 protein or protein fragments. As the present invention provides a means to purify large amount of BAD-1 protein or protein fragments, and BAD-1 protein or protein fragments are proven to be an important antigen against the fungus of *Blastomyces dermatitidis*, the highly purified BAD-1 protein or protein fragments are potent biomarkers for diagnostic blastomycosis. The high purity of BAD-1 protein or protein fragments may offer unprecedented specificity and sensitivity to the diagnostic method.

As used herein, the term "patient" refers to a human or non-human mammalian patient at danger of suffering from a condition of Blastomycosis.

As used herein, the term "body fluid" refers to liquids originating from inside the bodies of living mammals. The body fluid includes fluids that are excreted or secreted from the body as well as body water that normally is not. The examples of body fluids may include urine, amniotic fluid, aqueous humour and vitreous humour, bile, blood serum, breast milk, cerebrospinal fluid, cerumen (earwax), chyle, endolymph and perilymph, feces (diarrhea), female ejaculate, gastric acid, gastric juice, lymph, mucus (including nasal drainage and phlegm), peritoneal fluid, pleural fluid, pus, saliva, sebum (skin oil), semen, sweat, synovial fluid, tears, vaginal secretion, vomit, urine, and others.

The present diagnostic method is generally applied to mammals. A mammal may be human or non-human mammal. For instance, the present invention is suitable for commercially important farm animals, such as cows, horses, pigs, rabbits, goats, and sheep. One may also wish to apply the present invention on companion animals, such as cats and dogs. In one embodiment, the present diagnostic method is applied to dogs.

Blastomycosis causes acute and chronic pneumonias and disseminated infection with cutaneous lesions as the major extrapulmonary manifestation. However, the vast majority of infected patients are asymptomatic or have mild respiratory symptoms that are not diagnosed as being caused by a fungal infection. Rarely, patients develop severe pulmonary infection that progresses to acute respiratory distress syndrome (ARDS), which has a high mortality rate. The sensitivity and specificity of a urinary or other body fluid antigen test to aid diagnostic Blastomycosis is dependent on the purity of the BAD-1 protein or protein fragments, as the antigen.

The current available urinary or other body fluid antigen test with BAD-1 protein or protein fragments having low purity is not specific and is positive in patients who have histoplasmosis as well as blastomycosis. Further, currently available antibody assays remain nonspecific and insensitive due to the same reason of lacking highly purified antigen. The confirmatory diagnostic test is still growth of the organism in culture, which is a time-consuming process.

Applicants envision that the highly purified BAD-1 protein or protein fragments provided in the present invention would offer diagnostic methods of high sensitivity, high specificity, and less detection time to urinary or other body fluid antigen test essays and antigen assays.

In one embodiment, the present invention is a detection method in which the protein preparations of the present invention are used in an antibody detection method. Urinary or other body fluid antigen test assays and antigen assays are well-known in the art. For instance, examples of antigen assays may include, but are not limited to, immunoassay (including enzyme immunoassay), radioimmunoassay, Spectrophotometry assay, Enzyme-linked immunosorbent assay (ELISA), Immune-chromatographic assay, or even PCR detection methods, etc.

In its simplest form, the assay is formatted with antigen as the target or bait to detect appropriately specific antibodies in sera of infected patient samples. This reaction is followed by anti-serum against the appropriate species, which is bound to a fluorescent tag or enzyme for detection. Alternatively, the protein antigen in question here is sought by using specific antiserum or monoclonal to detect its presence. The antigen-antibody complex would be detected as above with antiserum raised against the species in question. PCR based methods may be used to detect the protein in biological fluids, if aptamers specific for the protein sequence were available.

Applicants' initial results show that the diagnostic method using native BAD-1 protein as a biomarker has at least 99% sensitivity. The specificity is found to be at least 60%, but usually much higher. Further, after the identification of an EGF (epidermal growth factor) binding domain on the C-terminal end of the native BAD-1 protein, Applicants hypothesized that the EGF domain may be the cause of the sensitivity problem since a number of microbials and other cells express EGF receptor. As the EGF-deleted BAD-1 protein fragment still binds divalent cations, such as nickel, the EGF-deleted BAD-1 protein fragment may be easily purified in large quantity. Applicants' subsequent results show that a diagnostic method using the EGF-deleted BAD-1 protein fragment after removal of the C-terminal end of the native BAD-1 protein improves sensitivity to at least 90% with a slight loss in specificity.

In another embodiment, the present invention is directed to a diagnostic kit using diagnostic methods discussed above. In one embodiment, a diagnostic kit for detecting an infection of *Blastomyces dermatitidis* in a mammalian patient would comprise highly pure native BAD-1 protein or protein fragments, in some embodiments attached to a substrate such as alkaline phosphatase. The most preferred components of the kit reaction would include BAD-1 proteins or protein fragments as antigens purified as described above, a solid support or a substrate, patient antiserum (which would be supplied by the patient), and a means of signal generation and detection. The means of signal generation and detection may include, but not limited to, anti-human immunoglobulin linked to an enzyme or fluorescent tag, alkaline phosphatase, horse-radish peroxidase, or fluorescent signal. The means of signal generation and detection may further include, but not limited to, microscopy, protein immunostaining, Protein immunoprecipitation, Immunoelectrophoresis, Immunoblotting, BCA Protein Assay (to measure protein concentrations), Western blot, Spectrophotometry, or Enzyme assay. In such an assay, the protein could typically be linked to any solid support including a plate, bead, agarose matrix, etc.

One suitable kit may include the components of a direct fluorescent-antibody kit, such as Vet-IF (Cell Labs), IMAGEN (Celltech), Chlamydia-Direct IF (Bio Merieux), antigen detection enzyme-linked immunosorbent assay (ELISA) kits, such as Clearview (Unipath), Surecell (Kodak), Pathfinder (Kallestad), Chlamydia-EIA (Pharmacia), Chlamydiazyme (Abbott), and IDEIA (Celltech).

EXAMPLES

Materials

7H10 Medium:

Middlebrook 7H10 agar (Sigma, St. Louis, Mo.) with 10% oleic acid-albumin-dextrose-catalase complex (OADC).

HMM Medium:

F-12 nutrient mixture with I-glutamine, with phenol red, without sodium bicarbonate (Gibco BRL, Gaithersburg, Md.), supplemented with (per liter) 18.2 g of glucose, 1.0 g of glutamic acid, 84 mg of cystine, and 5.96 g of HEPES, adjusted to pH 7.5.

OADC Complex:

500 ml $dH_2O$, 4.25 g NaCl, 25 g Bovine Serum Albumin Fraction V, 10 g D-dextrose, 20 mg catalase, and 0.25 g Oleic acid; Dissolve NaCl and BSA in $dH_2O$; add D-dextrose, catalase, and oleic acid.

Protocol for Extraction of Native BAD1 from *Blastomyces* Yeast

1. Cell Culture

*Blastomyces dermatitidis* strain 26199 (ATCC) was inoculated from a fresh stock slant culture of 7H10 medium into 50 ml of HMM medium with penicillin/streptomycin in a 250 ml Erlenmeyer flask. This starter culture was incubated at 200 rpm at 37° C. until the culture became thick (about 2 days). The turbid culture was expanded by splitting into two 2-liter flasks, each containing 0.5 liters of HMM with penicillin/streptomycin and culturing for an additional 5 days at 37° C. 7H10 medium includes Middlebrook 7H10 agar (Sigma, St. Louis, Mo.) with 10% oleic acid-albumin-dextrose-catalase complex (OADC). OADC included 500 ml $dH_2O$, 4.25 g NaCl, 25 g bovine serum albumin fraction V, 10 g D-dextrose, 20 mg catalase, and 0.25 g oleic acid. HMM includes F-12 nutrient mixture with L-glutamine, with phenol red, without sodium bicarbonate (Gibco BRL, Gaithersburg, Md.), supplemented with (per liter) 18.2 g of glucose, 1.0 g of glutamic acid, 84 mg of cystine, and 5.96 g of HEPES, adjusted to pH 7.5.

2. Isolation of BAD-1

Yeast were collected by centrifugation at 4000×g for 15 min. The supernatant was discarded and the pellet transferred into 50 ml falcon tubes and washed once, briefly, in PBS (50 mM $Na^+$-phosphate buffer, pH 8, 150 mM NaCl). The yeast were spun down immediately and the yeast pellet saved. Two volumes of distilled water were added to the pellet and the pellet was resuspended. The yeast slurry was rocked at a rate to maintain an even slurry of yeast for 1 hour at 4° C. After the incubation, the yeast were pelleted at 4000×g for 5 min. The supernatant was collected and the water wash procedure was repeated twice more. All water extracts were pooled and filter sterilized to remove residual yeast. Pooled extracts often contain >75 micrograms BAD-1/ml and are only moderately contaminated by non-BAD-1 *Blastomyces* proteins that were removed in subsequent steps below.

To enrich for BAD-1 protein (with or without an engineered His tag), 10 ml of nickel resin (Ni-NTA) were prepared for every liter of original yeast culture volume. For every 1 liter of culture of 26199 yeast required a column containing 10 ml packed bed volume of Ni-NTA resin. The Ni-NTA resin was washed three times with PBS. Phosphate buffer, pH8 and NaCl are added to the buffered water extract containing BAD-1 to final concentrations of 20 mM and 300 mM respectively. The Ni-NTA resin and the buffered water extract containing BAD-1 were combined and agitated gently for 1 hour at 4° C. The slurry was then poured through a funnel into a column fitted with a frit, allowing the resin to pack the column evenly.

The first few milliliters of pass-though were collected and cycled back through the funnel to rinse residual resin into the column. The columns were then washed with 10 volumes of 20 mM phosphate buffer containing 300 mM NaCl. Because the BAD-1 protein being isolated lacked a 6×His tag, a lower stringency, imidazole-free PBS buffer was used to wash the loaded columns. A sample of the wash buffer was retained for analysis of BAD-1 content and the remainder discarded. The columns were eluted with 3 column volumes of 250 mM imidazole in 20 mM phosphate buffer containing 300 mM NaCl.

3. Extraction of Mannoproteins

To extract contaminating mannoproteins from BAD-1, PBS-washed concanavalin-agarose resin (Sigma, St. Louis, Mo.) and $MgCl_2$ and $CaCl_2$ salts to final concentrations of 1 mM each and $MnCl_2$ to a final concentration of 0.1 mM were added to the BAD-1 eluate. One milligram of concanavalin-agaroseresin extracts approximately 12 micrograms of contaminating mannoprotein. Typically, between 20-50 mg of resin were required to clean up a BAD-1 sample derived from 1 liter of original culture volume. Optimal quantity of concanavalin-agarose resin should be determined empirically, contingent upon variations in scaling-up and application. The samples were incubated for 30 min, and the resin spun off prior to removing imidazole.

Imidazole was removed from the collected concanavalin-agarose resin eluate immediately by dialyzing against $dH_2O$ using dialysis tubing with a molecular weight cut off of 50,000 Da. The samples were dialyzed with three changes of $dH_2O$ with at least one hour between changes. The dialyzed samples were concentrated using a Centriprep® unit (Millipore Corp., Billerica, Mass.), reducing the volume to <2 ml. Concentrations of BAD-1 were measured on a spectrophotometer at $A_{280}$ using an absorption coefficient of 0.15 (0.15 mg/ml BAD-1 protein has an $A_{280}$ of 1.0 due to exceptionally high tryptophan content). The samples were sterilized with a syringe filter unit and preserved with azide to 0.1% for long-term storage at 4° C. or frozen for long-term storage at −20° C. At concentrations above 4 mg/ml, and in the presence of azide, sterilized BAD-1 remains quite stable for years at 4° C. For anticipated diagnostic uses of the BAD-1 protein, storage at −20° C. may be preferred. Alternatively, concanavalin extractions may be performed subsequent to imidazole removal to minimize the influence of high imidazole concentrations upon this extraction process.

4. Results and Discussion

Nickel Agarose Purification of BAD-1 and Carbohydrate Contaminant Removal

The BAD-1 adhesin of *Blastomyces dermatitidis* is of interest due to its indispensible role in *B. dermatitidis* virulence, its highly antigenic tandem-repeat sequences, and the fact that said tandem-repeats are distinctly unique to *B. dermatitidis*, with no reported homologues amongst the dimorphic fungi. During yeast-phase culture of *B. dermati-*

*tidis*, the 120 kDa BAD-1 adhesin accumulates upon the outer cell walls of yeast in a fashion that has been found to be calcium-dependent. This characteristic allows the extraction of BAD-1 into the aqueous by depletion of divalent cations. Our protocol accomplishes this by washing pelleted yeast once, briefly, in phosphate buffer prior to serial extraction into $dH_2O$ at 4° C. This material is impure, but BAD-1 is the principal protein component (FIG. 1, lane 2).

BAD-1 has a significant affinity for polysaccharide, in particular the polysaccharide chitin present in fungal cell walls. BAD-1 may also interact with mannoprotein components of the cell wall, and these components appear to co-purify with BAD-1. While the BAD-1 adhesin is unique to *B. dermatitidis*, it is known that some cell surface mannoproteins are conserved amongst the dimorphic fungi. These components could be responsible for observed cross-reactivity of sera from patients with blastomycosis, histoplasmosis, valley fever, etc. The challenge, therefore, is to enrich BAD-1 while minimizing the amount of cross-reactive mannoprotein present in the final product.

Figure 2:
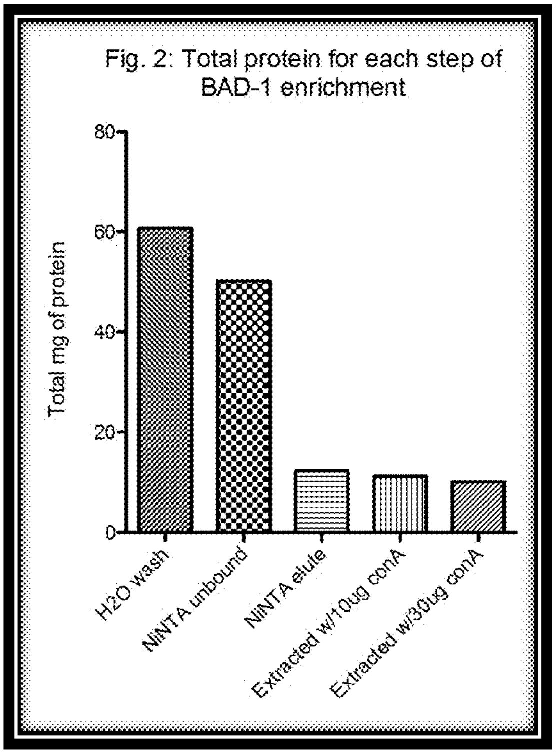
FIG. 2 is graph showing total protein at each step of enrichment process. Protein quantity was estimated by measuring absorbance at $A_{280}$ for each step of the BAD-1 enrichment process. Absorbance was measured prior to adjustment for the empirically determined absorbance coefficient of BAD-1.
Figure 3:
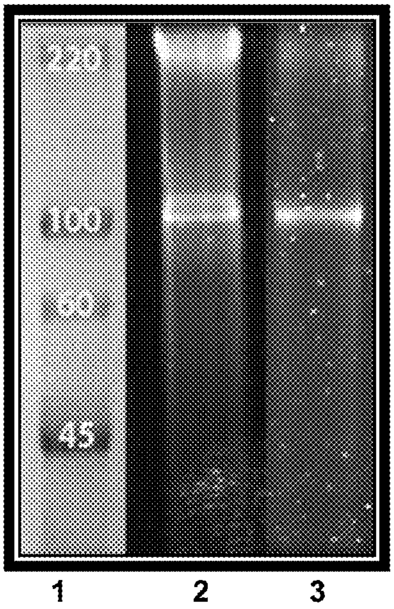
FIG. 3 is a graph of SDS-PAGE analysis showing relative carbohydrate removal by concanavalin A (ConA)-agarose resin purification. Ten percent PAGE gel of BAD-1 enriched fractions (images collated from 2 separate gels) were stained for carbohydrate with ProQ® Emerald stain to visualize carbohydrates/glycoproteins. Lane 1—MW standard (kDa); lane 2—Ni-NTA elution fraction containing BAD-1; and lane 3—BAD-1 after extraction of contaminants via concanavalin-agarose resin (10 μg). BAD-1 migrates at 120 kDa, and primary mannoprotein contaminants migrate at ~220 kDa. Note that most of the 220 kDa contaminant has been removed.

Under the conditions of the protocol disclosed herein, Ni-NTA resin binds BAD-1 with sufficient affinity that BAD-1 protein in not found in the unbound fraction or washes (FIG. 1, lane 3). This ability of BAD-1 to bind Ni-containing resin permits the removal of a significant amount of non-specific protein (FIG. 2, column 2). It is further contemplated that additional divalent cation-containing resins (for example, manganese, zinc, or copper) or other cation-supporting matrices may be used in the present disclosure along with or in place of Ni-resin. BAD-1 enriched by the current Ni-resin protocol, when examined by PAGE gel/Coomassie staining, shows no appreciable contaminating material (FIG. 1, lane 4), but cell wall glycoproteins rich in polymannose modifications are known to stain poorly by conventional methods. Optimally, detection of these contaminating glycoproteins is accomplished by carbohydrate specific stain, for example, ProQ Emerald staining kit, (Invitrogen) as is shown in FIG. 3 or Phenol Sulfuric Acid (PSA) assay in FIG. 4 following conventional techniques.

Figure 4:
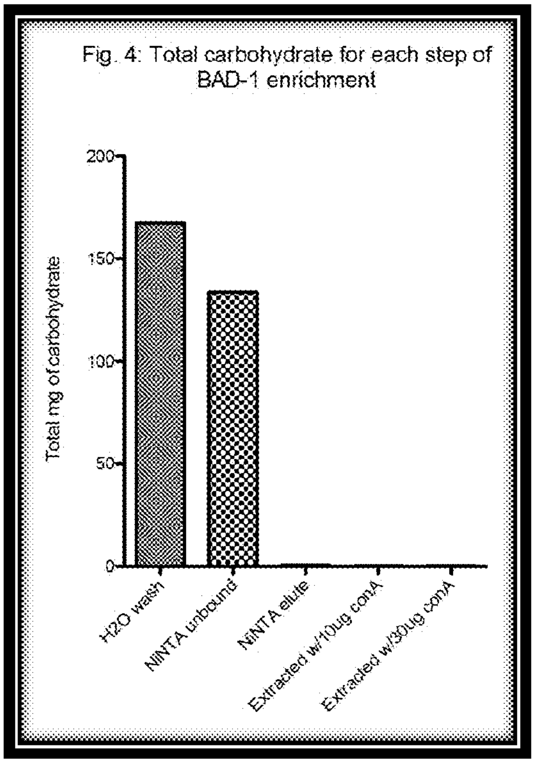
FIG. 4 is a graph showing total carbohydrate at each step of the enrichment process. Phenol Sulfuric Acid (PSA) was used to determine total carbohydrate present in each step of the BAD-1 enrichment process. Columns 3-5 are represented in FIG. 5 at a more proportionate range of carbohydrate concentration.

The Ni-resin enrichment step described removes approximately 99.8% of the carbohydrate present in the $dH_2O$ extracts (FIG. 4). Most of the material removed in this fashion is low molecular weight mannan. Elimination of contaminating mannan at this stage of the protocol is important, as mannan is a potent inhibitor of the concanavalin-agarose resin and severely interferes with the capacity of concanavalin-agarose resin to clean up the highly antigenic, high-molecular weight mannoprotein that remains as a contaminant (FIG. 3, lane 2, band migrating at ~220 kDa).

Figure 5:
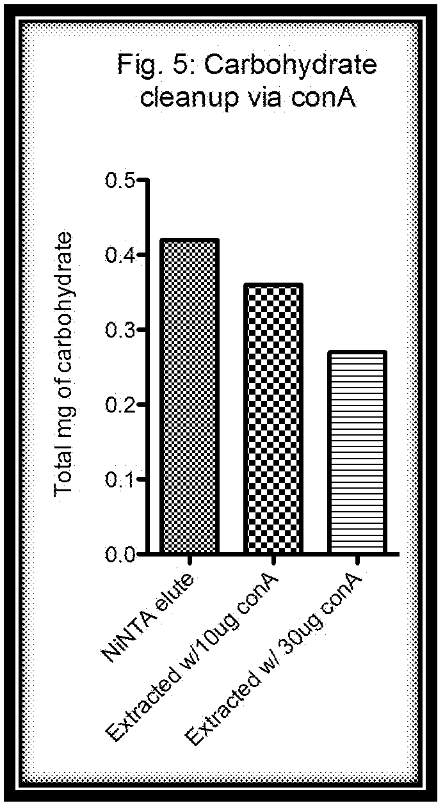
FIG. 5 is a graph showing total carbohydrate at each step of enrichment process. Blow up of lanes 3-5 of FIG. 4.

Incubation of the Ni-resin eluate fraction with 10 μg of concanavalin-agarose resin results in the loss of less than 10% of the $A_{280}$ determined protein (FIG. 2, column 4). However, this treatment decreases total carbohydrate in the sample by about 14% (FIG. 5, column 2). Incubating the Ni-resin eluate fraction with 30 μg of concanavalin-agarose resin resulted in an 18% lower overall yield of protein by $A_{280}$ (FIG. 2, column 5), but decreased total carbohydrate contaminant by 40% (FIG. 5, column 3). It is not known if contaminating carbohydrate can be completely eliminated. However, for the purposes of developing a diagnostic antigen, it is preferable to eliminate contaminating carbohydrates, preferably rendering an antigen 100% free of contaminating carbohydrates.

REFERENCES

1. U.S. Pat. No. 6,248,322 B1
2. U.S. Pat. No. 5,302,530
3. U.S. Pat. No. 5,093,118
4. Bradsher R W, Chapman S W, Pappas P G. Blastomycosis. *Infect Dis Clin North Am.* 2003; 17:21-40.
5. Brandhorst, et al. Calcium Binding by the Essential Virulence Factor BAD-1 of *Blastomyces dermatitidis*. J. Biol. Chem. 280(51), 42156-63, 2005.
6. Newman, S. L., Chaturvedi, S., and Klein, B. S. (1995) *J. Immunol.* 154, 753-761
7. Finkel-Jimenez, B., Wüthrich, M., Brandhorst, T., and Klein, B. S. (2001) *J. Immunol.* 166, 2665-2673.
8. Brandhorst, T. T., Finkel-Jimenez, B., Wüthrich, M., Warner, T., and Klein, B. S. (2004) *J. Immunol.* 173, 7444-7453
9. Finkel-Jimenez, B., Wüthrich, and Klein, B. S. (2002) *J. Immunol.* 168, 5746-5755
10. Rippon J W. *Medical Mycology: The pathogenic fungi and the pathogenic actinomycetes.* 3rd ed. Philadelphia, Pa.: W. B. Saunders; 1988. Blastomycosis; pp. 474-505
11. Mongkolrattanothai K, Peev M, Wheat L J, Marcinak J. Urine antigen detection of blastomycosis in pediatric patients. *Pediatr Infect Dis J.* 2006; 25:1076-1078
12. Hogan et al. (1995) J. Biol. Chem. 270, 30725-32
13. Brandhorst T, Wüthrich M, Finkel-Jimenez B, Klein B (2003) A C-terminal EGF-like domain governs BAD1 localization to the yeast surface and fungal adherence to phagocytes, but is dispensable in immune modulation and pathogenicity of *Blastomyces dermatitidis. Mol Microbiol* 48: 53-65

We claim:

1. A method for the purification of native *Blastomyces* Adhesion 1 (BAD-1) protein or protein fragments, comprising the steps of:

(a) obtaining a native BAD-1 protein or protein fragment-containing solution; and (b) purifying the native BAD-1 protein or protein fragments from the solution in the absence of affinity tags, consisting essentially of the steps of:

(i) combining the native BAD-1 protein or protein fragments-containing solution with a suitable divalent cation, (ii) washing the suitable divalent cation with an imidazole-free buffer to remove unbound matter, and (iii) eluting the native BAD-1 protein or protein fragments with an imidazole-containing buffer from a nickel-chelating resin.

2. The method of claim 1, wherein the native BAD-1 protein or protein fragment-containing solution is obtained by the steps of:

(a1) culturing a population of microbes expressing native BAD-1 protein or protein fragment in a culture medium;

(a2) collecting the population of microbes containing the native BAD-1 protein or protein fragment from the culture medium, and (a3) isolating the native BAD-1 protein or protein fragment from the microbes.

3. The method of claim 1, wherein the suitable divalent cation is a nickel-chelating resin.

4. The method of claim 2, wherein the microbes comprise *Blastomyces dermatitidis.*

5. The method of claim 4, wherein *Blastomyces dermatitidis* is selected from the group consisting of ATCC native strains of 26199, 14081, and ER-3.

6. The method of claim 1, wherein step (a) comprises extraction of the BAD-1 protein or protein fragments from yeast cell surfaces using a low osmotic strength and divalent cation-free buffer.

7. The method of claim 1, wherein the BAD-1 protein fragments are derived from one or more recombinant BAD-1 proteins.

8. A method for the purification of native *Blastomyces* Adhesion 1 (BAD-1) protein or protein fragments, comprising the steps of:

(a) obtaining a native BAD-1 protein or protein fragment-containing solution; and (b) purifying the native BAD-1 protein or protein fragments from the solution in the absence of affinity tags, consisting essentially of the steps of:

(i) combining the native BAD-1 protein or protein fragments-containing solution with a suitable divalent cation, (ii) washing the suitable divalent cation with an imidazole-free buffer to remove unbound matter, and (iii) eluting the native BAD-1 protein or protein fragments with an imidazole-containing buffer from a nickel-chelating resin, (iv) extracting contaminating mannoproteins from the eluted native BAD-1 protein or protein fragments.

9. A method for the purification of native *Blastomyces* Adhesion 1 (BAD-1) protein or protein fragments, comprising the steps of:

(a) obtaining a native BAD-1 protein or protein fragment-containing solution; and (b) purifying the native BAD-1 protein or protein fragments from the solution in the absence of affinity tags, consisting essentially of the steps of:

(i) combining the native BAD-1 protein or protein fragments-containing solution with a suitable divalent cation, (ii) washing the suitable divalent cation with an imidazole-free buffer to remove unbound matter, and (iii) eluting the native BAD-1 protein or protein fragments with an imidazole-containing buffer from a nickel-chelating resin, (iv) extracting contaminating mannoproteins from the eluted native BAD-1 protein or protein fragments by treating the eluted native BAD-1 protein or protein fragments with concanavalin-agarose resin.

* * * * *

SEQUENCE LISTING

```
<160> NUMBER OF SEQ ID NOS: 5

<210> SEQ ID NO 1
<211> LENGTH: 1146
<212> TYPE: PRT
<213> ORGANISM: Blastomyces adhesin 1 (26199 strain)

<400> SEQUENCE: 1

Met Pro Asp Ile Lys Ser Val Ser Ser Ile Leu Leu Leu Val Ser Ser
1               5                   10                  15

Ser Leu Val Ala Ala His Pro Gly Ala Arg Tyr Pro Arg Asp Asp Lys
            20                  25                  30

Tyr Pro Val Asn Val Lys Tyr Ser Glu His Phe His His Pro Lys Cys
        35                  40                  45
```

-continued

```
Asp Trp His Leu Trp Asp Gln Trp Cys Asn Gly Asp Gly His Lys His
    50                  55                  60

Phe Tyr Asp Cys Gly Trp Gly Leu Thr His Pro Asn Tyr Asn Tyr Arg
65                  70                  75                  80

Leu Trp Lys Tyr Trp Cys Asp Thr Lys Val His Tyr Asn Cys Glu Leu
                85                  90                  95

Asp Glu Ser His Leu Lys Tyr Asp Ala Gly Leu Phe Lys Ser Leu Cys
            100                 105                 110

Thr Gly Pro Gly Lys His Leu Tyr Asp Cys Asp Trp Pro Thr Ser His
        115                 120                 125

Val Ser Tyr Ser Trp Tyr Leu His Asp Tyr Leu Cys Gly Asn Gly His
    130                 135                 140

His Pro Tyr Asp Cys Glu Leu Asp Ser Ser His Glu Asp Tyr Ser Trp
145                 150                 155                 160

Pro Leu Trp Phe Lys Trp Cys Ser Gly His Gly Arg His Phe Tyr Asp
                165                 170                 175

Cys Lys Trp Asp Asn Asp His Glu Lys Tyr Asp Trp Pro Leu Trp Gln
            180                 185                 190

Tyr Trp Cys Gly Ser His Asp Lys Asp Pro Tyr Asn Cys Asp Trp Asp
        195                 200                 205

Lys Phe His Glu Lys Tyr Asp Trp Glu Leu Trp Asn Lys Trp Cys Lys
    210                 215                 220

Asp Pro Tyr Asn Cys Glu Trp Asp Ser Ser His Glu Lys Tyr Asp Trp
225                 230                 235                 240

Glu Leu Trp Asn Lys Trp Cys Lys Asp Pro Tyr Asn Cys Glu Trp Asn
                245                 250                 255

Ser Phe His Glu Lys Tyr Asp Trp Glu Leu Trp Asn Lys Trp Cys Lys
            260                 265                 270

Asp Ser Tyr Asn Cys Glu Trp Asp Ser Ser His Glu Lys Tyr Asp Trp
        275                 280                 285

Glu Leu Trp Asn Lys Trp Cys Lys Asp Pro Tyr Asn Cys Asp Trp Asp
    290                 295                 300

Ser Ser His Glu Lys Phe Asp Trp Gly Leu Trp Ser His Trp Cys Asn
305                 310                 315                 320

Asp Tyr Asp Lys Tyr Pro Tyr Asn Cys Glu Trp Asp Ser Ser His Lys
                325                 330                 335

Lys Tyr Asp Leu Thr Leu Trp Asn Arg Trp Cys Ser Ser Tyr Asp Lys
            340                 345                 350

Asp Pro Tyr Lys Cys Asp Trp Asp Leu Trp Asn Gln Leu Cys Ser Gly
        355                 360                 365

Asn Gly His His Phe Tyr Asp Cys Asp Trp Asp Val Ser Tyr Pro Gly
    370                 375                 380

Tyr Asp Ser His Leu Trp Asp Leu Leu Cys Thr Asn Asn Pro Tyr Asn
385                 390                 395                 400

Cys Glu Trp Asp Ser Ser His Glu Lys Tyr Asp Trp Glu Leu Trp Asp
                405                 410                 415

Lys Trp Cys Lys Asp Pro Tyr Asn Cys Asp Trp Asp Ser Ser His Glu
            420                 425                 430

Lys Tyr Asp Trp Asp Leu Trp Asn Lys Trp Cys Lys Asp Pro Tyr Asn
        435                 440                 445

Cys Glu Trp Asp Ser Ser His Glu Lys Tyr Asp Trp Glu Leu Trp Asp
    450                 455                 460

Lys Trp Cys Lys Asp Pro Tyr Asn Cys Asp Trp Asp Ser Ser His Glu
```

-continued

```
465                 470                 475                 480

Lys Tyr Asp Trp Asp Leu Trp Asn Lys Trp Cys Lys Asp Pro Tyr Asn
                485                 490                 495

Cys Glu Trp Asp Ser Ser His Glu Lys Tyr Asp Trp Glu Leu Trp Asp
            500                 505                 510

Lys Trp Cys Lys Asp Pro Tyr Asn Cys Glu Trp Asp Ser Ser His Glu
        515                 520                 525

Lys Tyr Asp Trp Lys Leu Trp Asp Lys Trp Cys Lys Asp Phe Tyr Asn
    530                 535                 540

Cys Glu Trp Asp Ser Ser His Glu Lys Tyr Asp Trp Glu Leu Trp Asp
545                 550                 555                 560

Lys Trp Cys Lys Asp Ser Tyr Asn Cys Asp Trp Asp Lys Phe His Glu
                565                 570                 575

Lys Tyr Asp Trp Glu Leu Trp Asp Lys Trp Cys Lys Asp Ser Tyr Asn
            580                 585                 590

Cys Asp Trp Asp Lys Phe His Glu Lys Tyr Asp Trp Asp Leu Trp Asn
        595                 600                 605

Lys Trp Cys Lys Asp Ser Tyr Asn Cys Asp Trp Asp Lys Phe His Glu
    610                 615                 620

Lys Tyr Asp Trp Glu Leu Trp Asp Lys Trp Cys Lys Asp Ser Tyr Asn
625                 630                 635                 640

Cys Asp Trp Asp Lys Phe His Glu Lys Tyr Asp Trp Glu Leu Trp Asp
                645                 650                 655

Lys Trp Cys Lys Asp Phe Tyr Asn Cys Glu Trp Asp Ser Ser His Glu
            660                 665                 670

Lys Tyr Asp Trp Glu Leu Trp Asp Lys Trp Cys Lys Asp Pro Tyr Asn
        675                 680                 685

Cys Glu Trp Asp Ser Ser His Glu Lys Tyr Asp Trp Glu Leu Trp Asp
    690                 695                 700

Lys Trp Cys Lys Asp Phe Tyr Asn Cys Asp Trp Asp Lys Phe His Glu
705                 710                 715                 720

Lys Tyr Asp Trp Val Leu Trp Asn Lys Trp Cys Lys Asp Pro Tyr Asn
                725                 730                 735

Cys Glu Trp Asp Ser Ser His Glu Lys Tyr Asp Trp Glu Leu Trp Asp
            740                 745                 750

Lys Trp Cys Lys Asp Pro Tyr Asn Cys Asp Trp Asp Lys Phe His Glu
        755                 760                 765

Lys Tyr Asp Trp Asp Leu Trp Asn Lys Trp Cys Lys Asp Pro Tyr Asn
    770                 775                 780

Cys Glu Trp Asp Ser Ser His Glu Lys Tyr Asp Trp Glu Leu Trp Asp
785                 790                 795                 800

Lys Trp Cys Lys Asp Pro Tyr Asn Cys Glu Trp Asp Ser Ser His Glu
                805                 810                 815

Lys Tyr Asp Trp Lys Leu Trp Asp Lys Trp Cys Lys Asp Phe Tyr Asn
            820                 825                 830

Cys Glu Trp Asp Ser Ser His Glu Lys Tyr Asp Trp Glu Leu Trp Asp
        835                 840                 845

Lys Trp Cys Lys Asp Pro Tyr Asn Cys Glu Trp Asp Ser Ser His Glu
    850                 855                 860

Lys Tyr Asp Trp Glu Leu Trp Asp Lys Trp Cys Lys Asp Pro Tyr Asn
865                 870                 875                 880

Cys Glu Trp Asp Ser Ser His Glu Lys Tyr Asp Trp Glu Leu Trp Asn
                885                 890                 895
```

-continued

Lys Trp Cys Lys Asp Pro Tyr Asn Cys Glu Trp Asp Ser Ser His Glu
900 905 910

Lys Tyr Asp Trp Glu Leu Trp Asp Lys Trp Cys Lys Asp Phe Tyr Asn
915 920 925

Cys Glu Trp Asp Ser Ser His Glu Lys Tyr Asp Trp Glu Leu Trp Asp
930 935 940

Lys Trp Cys Lys Asp Pro Tyr Asn Cys Glu Trp Asp Ser Ser His Glu
945 950 955 960

Lys Tyr Asp Trp Glu Leu Trp Asp Lys Trp Cys Lys Asp Phe Tyr Asn
965 970 975

Cys Glu Trp Asp Ser Ser His Glu Lys Tyr Asp Trp Lys Leu Trp Asn
980 985 990

Lys Trp Cys Lys Asp Phe Tyr Asn Cys Glu Trp Asp Ser Ser His Glu
995 1000 1005

Lys Tyr Asp Trp Lys Leu Trp Asn Lys Trp Cys Lys Asp Phe Tyr
1010 1015 1020

Asn Cys Glu Trp Asp Ser Ser His Glu Lys Tyr Asp Trp Glu Leu
1025 1030 1035

Trp Asn Lys Trp Cys Asn Lys His Asp Glu His Asp Lys His Pro
1040 1045 1050

Trp Cys Pro Val Cys Asp Pro Leu Ser Gly Ala Asn Arg Cys His
1055 1060 1065

Pro Thr Thr Ser Cys Ile Gly Thr Gly His Ser Tyr Tyr Cys Ala
1070 1075 1080

Cys Arg Ala Gly Tyr Lys Ser Ser His Tyr Ser His Asp His Lys
1085 1090 1095

Asn Phe Arg Leu Pro Phe Pro Gly Tyr Glu Phe Leu Val Phe Thr
1100 1105 1110

Pro Pro Gly Thr Glu Cys Asp Val Leu Cys Asp Gly Tyr Pro His
1115 1120 1125

Lys Pro Ala His Lys Leu Cys Ser Glu Val Lys Val His Asn Tyr
1130 1135 1140

Cys Glu Pro
1145

<210> SEQ ID NO 2
<211> LENGTH: 699
<212> TYPE: PRT
<213> ORGANISM: Blastomyces adhesin 1 (14081 strain)

<400> SEQUENCE: 2

Met Pro Asp Ile Lys Ser Val Ser Ser Ile Leu Leu Leu Val Ser Ser
1 5 10 15

Ser Leu Val Ala Ala Arg Pro Gly Ala Arg Tyr Pro Arg Asp Asp Lys
20 25 30

Tyr Pro Val Asp Val Lys Tyr Asn Gly His Phe Gly His Pro Lys Cys
35 40 45

Asp Trp His Leu Trp Asp Gln Trp Cys Asn Gly Asp Gly His Lys His
50 55 60

Phe Tyr Asp Cys Gly Trp Gly Leu Ser Asp Pro Lys Tyr Asn Tyr Asp
65 70 75 80

Leu Trp Ser Tyr Trp Cys Asp Thr Lys Gln His Tyr Asn Cys Glu Leu
85 90 95

Asp Glu Ser His Leu Lys Tyr Asp Ala Val Leu Trp Lys Ser Ser Cys

-continued

```
            100                 105                 110

Thr Gly His Gly Lys His Phe Tyr Asp Cys Asp Trp Asp Pro Ser His
        115                 120                 125

Gly Asp Tyr Ser Trp Tyr Leu Trp Asp Tyr Leu Cys Gly Asn Gly His
    130                 135                 140

His Pro Tyr Asp Cys Glu Leu Asp Asn Ser His Glu Asp Tyr Asn Trp
145                 150                 155                 160

Asn Leu Trp Phe Lys Trp Cys Ser Gly His Gly Arg His Phe Tyr Asp
                165                 170                 175

Cys Lys Trp Asp Asn Thr His Glu Lys Tyr Asp Trp Leu Leu Trp Gln
            180                 185                 190

Tyr Trp Cys Gly Ser Asn Gly Lys Asp Pro Tyr Asn Cys Asp Trp Asp
        195                 200                 205

Lys Ser His Glu Arg Tyr Asp Leu Asn Leu Trp Asn Gln Trp Cys Asn
    210                 215                 220

Lys Asp Tyr Tyr Ser Cys Glu Trp Asp Ser Leu His Glu Lys Phe Asn
225                 230                 235                 240

Trp Asp Leu Trp Asp His Trp Cys Asn Gly Tyr Asp Met Tyr Pro Tyr
                245                 250                 255

Asn Cys Glu Trp Asp Gln Ser His Glu Lys Tyr Asp Leu Thr Leu Trp
            260                 265                 270

Asn His Trp Cys Ser Ser Tyr Asp Lys Asp Pro Tyr Lys Cys Asp Trp
        275                 280                 285

Gly Leu Trp Asn Gly Leu Cys Ser Gly Asn Gly Lys His Phe Tyr Asp
    290                 295                 300

Cys Asp Trp Asp Asp Ser His Pro Gly Tyr Asp Pro His Leu Trp Asp
305                 310                 315                 320

Ile Leu Cys Thr Lys Asp Pro Tyr Asn Cys Asp Trp Asp Pro Ser His
                325                 330                 335

Glu Lys Tyr Asp Trp Glu Leu Trp Asn Lys Trp Cys Asn Lys Asp Pro
            340                 345                 350

Tyr Asn Cys Asp Trp Asp Pro Ser His Glu Lys Tyr Asp Trp Asp Leu
        355                 360                 365

Trp Asn Lys Trp Cys Lys Asp Pro Tyr Asn Cys Asp Trp Asp Pro Tyr
    370                 375                 380

His Glu Lys Tyr Asp Trp Asp Leu Trp Asn Lys Trp Cys Asn Lys Asp
385                 390                 395                 400

Pro Tyr Asn Cys Asp Trp Asp Pro Ser His Glu Lys Tyr Asp Leu Ser
                405                 410                 415

Leu Trp Asn Lys Trp Cys Lys Asp Pro Tyr Asn Cys Asp Trp Asp Pro
            420                 425                 430

Tyr His Glu Lys Tyr Asp Trp Asp Leu Trp Asn Lys Trp Cys Asn Lys
        435                 440                 445

Asp Pro Tyr Asn Cys Asp Trp Asp Pro Ser His Glu Lys Tyr Asp Trp
    450                 455                 460

Glu Leu Trp Asn Lys Trp Cys Asn Lys Asp Pro Tyr Asn Cys Asp Trp
465                 470                 475                 480

Asp Pro Tyr His Glu Lys Tyr Asp Trp Asp Leu Trp Asn Lys Trp Cys
                485                 490                 495

Asn Lys Asp Pro Tyr Asn Cys Asp Trp Asp Pro Ser His Glu Lys Tyr
            500                 505                 510

Asp Trp Asp Leu Trp Asn Lys Trp Cys Asn Lys Asp Pro Tyr Asn Cys
        515                 520                 525
```

-continued

Asp Trp Asp Pro Tyr His Glu Lys Tyr Asp Trp Asp Leu Trp Asn Lys
530 535 540

Trp Cys Asn Lys Asp Pro Tyr Asn Cys Asp Trp Asp Pro Tyr His Glu
545 550 555 560

Lys Tyr Asp Trp Asp Leu Trp Asn Lys Trp Cys Asn Lys Asp Pro Tyr
565 570 575

Asn Cys Asp Trp Asp Pro Ser His Glu Lys Tyr Asp Trp Asp Leu Trp
580 585 590

Ser Lys Trp Cys Asn Lys His Asp Glu His Asp Lys His Pro Leu Cys
595 600 605

Pro Val Cys Asp Pro Leu Ser Gly Lys Asn His Cys His Pro Thr Thr
610 615 620

Ser Cys Val Ser Thr Gly His His Tyr His Cys Ala Cys Arg Ala Gly
625 630 635 640

Tyr Lys Ala Ser His Tyr Ser His Asp His Lys His Phe Arg Met Pro
645 650 655

Val Lys Gly Tyr Glu Phe Leu Val Phe Thr Gly Pro His Thr Lys Cys
660 665 670

Asn Val Leu Cys Asp Gly Tyr Pro His Lys Pro Ala His Glu Leu Cys
675 680 685

Gly Glu Val Lys Val His Asn Tyr Cys Gly Pro
690 695

<210> SEQ ID NO 3
<211> LENGTH: 1171
<212> TYPE: PRT
<213> ORGANISM: Blastomyces adhesin 1 (ER-3 strain)

<400> SEQUENCE: 3

Met Pro Asp Ile Lys Ser Val Ser Ser Ile Leu Leu Leu Val Ser Ser
1 5 10 15

Ser Leu Val Ala Ala His Pro Gly Gly Ala Arg Tyr Pro Arg Asp Asp
20 25 30

Lys Tyr Pro Val Asn Val Lys Tyr Ser Glu His Phe Arg His Pro Lys
35 40 45

Cys Asp Trp His Leu Trp Asp Gln Trp Cys Asn Gly Asp Gly His Lys
50 55 60

His Phe Tyr Asp Cys Gly Trp Gly Leu Thr His Pro Asn Tyr Asn Tyr
65 70 75 80

Arg Leu Trp Lys Tyr Trp Cys Asp Thr Lys Val His Tyr Asn Cys Glu
85 90 95

Leu Asp Glu Ser His Leu Lys Tyr Asp Ala Gly Leu Phe Lys Ser Leu
100 105 110

Cys Thr Gly Pro Gly Lys His Leu Tyr Asp Cys Asp Trp Pro Thr Ser
115 120 125

His Val Ser Tyr Ser Trp Tyr Leu His Asp Tyr Leu Cys Gly Asn Gly
130 135 140

His His Pro Tyr Asp Cys Glu Leu Asp Ser Ser His Glu Asp Tyr Ser
145 150 155 160

Trp Pro Leu Trp Phe Lys Trp Cys Ser Gly His Gly Arg His Phe Tyr
165 170 175

Asp Cys Lys Trp Asp Asn Asp His Glu Lys Tyr Asp Trp Pro Leu Trp
180 185 190

Gln Tyr Trp Cys Gly Ser His Asp Lys Asp Pro Tyr Asn Cys Glu Trp

-continued

```
        195                 200                 205

Asp Ser Ser His Glu Lys Tyr Asp Trp Glu Leu Trp Asn Lys Trp Cys
    210                 215                 220

Lys Asp Pro Tyr Asn Cys Glu Trp Asp Ser Ser His Glu Lys Tyr Asp
225                 230                 235                 240

Trp Glu Leu Trp Asn Lys Trp Cys Lys Asp Pro Tyr Asn Cys Glu Trp
                245                 250                 255

Asp Ser Ser His Glu Lys Tyr Asp Trp Glu Leu Trp Asn Lys Trp Cys
            260                 265                 270

Lys Asp Ser Tyr Asn Cys Glu Trp Asp Ser Ser His Glu Lys Tyr Asp
        275                 280                 285

Trp Gly Leu Trp Asn Lys Trp Cys Lys Asp Phe Tyr Asn Cys Glu Trp
    290                 295                 300

Asp Ser Ser His Glu Lys Tyr Asp Trp Gly Leu Trp Asn Lys Trp Cys
305                 310                 315                 320

Lys Asp Pro Tyr Asn Cys Asp Trp Asp Ser Ser His Glu Lys Phe Asp
                325                 330                 335

Trp Gly Leu Trp Ser His Trp Cys Asn Asp Tyr Asp Lys Tyr Pro Tyr
            340                 345                 350

Asn Cys Glu Trp Asp Ser Ser His Lys Glu Tyr Asp Leu Thr Leu Trp
        355                 360                 365

Asn Leu Trp Cys Ser Ser Tyr Asp Lys Asp Pro Tyr Lys Cys Asp Trp
    370                 375                 380

Asp Leu Trp Asn Gln Leu Cys Ser Gly Asn Gly His His Phe Tyr Asp
385                 390                 395                 400

Cys Asp Trp Asp Val Ser Tyr Pro Gly Tyr Asp Ser His Leu Trp Asp
                405                 410                 415

Leu Leu Cys Thr Asn Asn Pro Tyr Asn Cys Glu Trp Asp Ser Ser His
            420                 425                 430

Glu Lys Tyr Asp Trp Asp Leu Trp Asn Lys Trp Cys Lys Asp Pro Tyr
        435                 440                 445

Asn Cys Asp Trp Asp Ser Ser His Glu Lys Tyr Asp Trp Glu Leu Trp
    450                 455                 460

Asp Lys Trp Cys Lys Asp Pro Tyr Asn Cys Asp Trp Asp Ser Ser His
465                 470                 475                 480

Glu Lys Tyr Asp Trp Asp Leu Trp Asn Lys Trp Cys Lys Asp Pro Tyr
                485                 490                 495

Asn Cys Glu Trp Asp Ser Ser His Glu Lys Tyr Asp Trp Glu Leu Trp
            500                 505                 510

Asp Lys Trp Cys Lys Asp Leu Tyr Asn Cys Glu Trp Asp Ser Ser His
        515                 520                 525

Glu Lys Tyr Asp Trp Lys Leu Trp Asp Lys Trp Cys Lys Asp Ser Tyr
    530                 535                 540

Asn Cys Asp Trp Asp Lys Phe His Glu Lys Tyr Asp Trp Glu Leu Trp
545                 550                 555                 560

Asn Lys Trp Cys Lys Asp Pro Tyr Asn Cys Glu Trp Asp Ser Ser His
                565                 570                 575

Glu Lys Tyr Asp Trp Glu Leu Trp Asp Lys Trp Cys Lys Asp Pro Tyr
            580                 585                 590

Asn Cys Glu Trp Asp Ser Ser His Glu Lys Tyr Asp Trp Glu Leu Trp
        595                 600                 605

Asp Lys Trp Cys Lys Asp Phe Tyr Asn Cys Glu Trp Asp Ser Ser His
    610                 615                 620
```

-continued

```
Glu Lys Tyr Asp Trp Glu Leu Trp Asp Lys Trp Cys Lys Asp Ser Tyr
625                 630                 635                 640

Asn Cys Asp Trp Asp Lys Phe His Glu Lys Tyr Asp Trp Glu Leu Trp
                645                 650                 655

Asp Lys Trp Cys Lys Asp Ser Tyr Asn Cys Asp Trp Asp Lys Phe His
            660                 665                 670

Glu Lys Tyr Asp Trp Asp Leu Trp Asn Lys Trp Cys Lys Asp Ser Tyr
        675                 680                 685

Asn Cys Asp Trp Asp Lys Phe His Glu Lys Tyr Asp Trp Glu Leu Trp
    690                 695                 700

Asp Lys Trp Cys Lys Asp Ser Tyr Asn Cys Asp Trp Asp Lys Phe His
705                 710                 715                 720

Glu Lys Tyr Asp Trp Lys Leu Trp Asp Lys Trp Cys Lys Asp Phe Tyr
                725                 730                 735

Asn Cys Glu Trp Asp Ser Ser His Glu Lys Tyr Asp Trp Glu Leu Trp
            740                 745                 750

Asp Lys Trp Cys Lys Asp Pro Tyr Asn Cys Glu Trp Asp Ser Ser His
        755                 760                 765

Glu Lys Tyr Asp Trp Glu Leu Trp Asp Lys Trp Cys Lys Asp Phe Tyr
    770                 775                 780

Asn Cys Asp Trp Asp Lys Phe His Glu Lys Tyr Asp Trp Asp Leu Trp
785                 790                 795                 800

Asn Lys Trp Cys Lys Asp Pro Tyr Asn Cys Glu Trp Asp Ser Ser His
                805                 810                 815

Glu Lys Tyr Asp Trp Glu Leu Trp Asp Lys Trp Cys Lys Asp Pro Tyr
            820                 825                 830

Asn Cys Glu Trp Asp Ser Ser His Glu Lys Tyr Asp Trp Glu Leu Trp
        835                 840                 845

Asn Lys Trp Cys Lys Asp Pro Tyr Asn Cys Glu Trp Asp Ser Ser His
    850                 855                 860

Glu Lys Tyr Asp Trp Glu Leu Trp Asp Lys Trp Cys Lys Asp Phe Tyr
865                 870                 875                 880

Asn Cys Glu Trp Asp Ser Ser His Glu Lys Tyr Asp Trp Glu Leu Trp
                885                 890                 895

Asp Lys Trp Cys Lys Asp Pro Tyr Asn Cys Glu Trp Asp Ser Ser His
            900                 905                 910

Glu Lys Tyr Asp Trp Lys Leu Trp Asp Lys Trp Cys Lys Asp Phe Tyr
        915                 920                 925

Asn Cys Glu Trp Asp Ser Ser His Glu Lys Tyr Asp Trp Glu Leu Trp
    930                 935                 940

Asp Lys Trp Cys Lys Asp Pro Tyr Asn Cys Glu Trp Asp Ser Ser His
945                 950                 955                 960

Glu Lys Tyr Asp Trp Glu Leu Trp Asp Lys Trp Cys Lys Asp Phe Tyr
                965                 970                 975

Asn Cys Glu Trp Asp Ser Ser His Glu Lys Tyr Asp Trp Lys Leu Trp
            980                 985                 990

Asn Lys Trp Cys Lys Asp Phe Tyr  Asn Cys Glu Trp Asp  Ser Ser His
        995                 1000                1005

Glu Lys  Tyr Asp Trp Lys Leu  Trp Asn Lys Trp Cys  Lys Asp Phe
    1010                1015                1020

Tyr Asn  Cys Glu Trp Asp Ser  Ser His Glu Lys Tyr  Asp Trp Lys
    1025                1030                1035
```

-continued

```
Leu Trp  Asn Lys Trp Cys Lys  Asp Phe Tyr Asn Cys  Glu Trp Asp
    1040                 1045                 1050

Ser Ser  His Glu Lys Tyr Asp  Trp Glu Leu Trp Asn  Lys Trp Cys
    1055                 1060                 1065

Asn Lys  His Asp Glu His Asp  Lys His Pro Trp Cys  Pro Val Cys
    1070                 1075                 1080

Asp Pro  Leu Ser Gly Ala Asn  Arg Cys His Pro Thr  Thr Ser Cys
    1085                 1090                 1095

Ile Gly  Thr Gly His Ser Tyr  Tyr Cys Ala Cys Arg  Ala Gly Tyr
    1100                 1105                 1110

Lys Ser  Ser His Tyr Ser His  Asp His Lys Asn Phe  Arg Leu Pro
    1115                 1120                 1125

Phe Pro  Gly Tyr Glu Phe Leu  Val Phe Thr Pro Pro  Gly Thr Glu
    1130                 1135                 1140

Cys Asp  Val Leu Cys Asp Gly  Tyr Pro His Lys Pro  Ala His Lys
    1145                 1150                 1155

Leu Cys  Ser Glu Val Lys Val  His Asn Tyr Cys Glu  Pro
    1160                 1165                 1170


<210> SEQ ID NO 4
<211> LENGTH: 1057
<212> TYPE: PRT
<213> ORGANISM: DELTA C-TERM

<400> SEQUENCE: 4

Met Pro Asp Ile Lys Ser Val Ser Ser Ile Leu Leu Leu Val Ser Ser
1               5                   10                  15

Ser Leu Val Ala Ala His Pro Gly Ala Arg Tyr Pro Arg Asp Asp Lys
            20                  25                  30

Tyr Pro Val Asn Val Lys Tyr Ser Glu His Phe His His Pro Lys Cys
        35                  40                  45

Asp Trp His Leu Trp Asp Gln Trp Cys Asn Gly Asp Gly His Lys His
    50                  55                  60

Phe Tyr Asp Cys Gly Trp Gly Leu Thr His Pro Asn Tyr Asn Tyr Arg
65                  70                  75                  80

Leu Trp Lys Tyr Trp Cys Asp Thr Lys Val His Tyr Asn Cys Glu Leu
                85                  90                  95

Asp Glu Ser His Leu Lys Tyr Asp Ala Gly Leu Phe Lys Ser Leu Cys
            100                 105                 110

Thr Gly Pro Gly Lys His Leu Tyr Asp Cys Asp Trp Pro Thr Ser His
        115                 120                 125

Val Ser Tyr Ser Trp Tyr Leu His Asp Tyr Leu Cys Gly Asn Gly His
    130                 135                 140

His Pro Tyr Asp Cys Glu Leu Asp Ser Ser His Glu Asp Tyr Ser Trp
145                 150                 155                 160

Pro Leu Trp Phe Lys Trp Cys Ser Gly His Gly Arg His Phe Tyr Asp
                165                 170                 175

Cys Lys Trp Asp Asn Asp His Glu Lys Tyr Asp Trp Pro Leu Trp Gln
            180                 185                 190

Tyr Trp Cys Gly Ser His Asp Lys Asp Pro Tyr Asn Cys Asp Trp Asp
        195                 200                 205

Lys Phe His Glu Lys Tyr Asp Trp Glu Leu Trp Asn Lys Trp Cys Lys
    210                 215                 220

Asp Pro Tyr Asn Cys Glu Trp Asp Ser Ser His Glu Lys Tyr Asp Trp
225                 230                 235                 240
```

```
Glu Leu Trp Asn Lys Trp Cys Lys Asp Pro Tyr Asn Cys Glu Trp Asn
                245                 250                 255

Ser Phe His Glu Lys Tyr Asp Trp Glu Leu Trp Asn Lys Trp Cys Lys
            260                 265                 270

Asp Ser Tyr Asn Cys Glu Trp Asp Ser Ser His Glu Lys Tyr Asp Trp
        275                 280                 285

Glu Leu Trp Asn Lys Trp Cys Lys Asp Pro Tyr Asn Cys Asp Trp Asp
    290                 295                 300

Ser Ser His Glu Lys Phe Asp Trp Gly Leu Trp Ser His Trp Cys Asn
305                 310                 315                 320

Asp Tyr Asp Lys Tyr Pro Tyr Asn Cys Glu Trp Asp Ser Ser His Lys
                325                 330                 335

Lys Tyr Asp Leu Thr Leu Trp Asn Arg Trp Cys Ser Ser Tyr Asp Lys
            340                 345                 350

Asp Pro Tyr Lys Cys Asp Trp Asp Leu Trp Asn Gln Leu Cys Ser Gly
        355                 360                 365

Asn Gly His His Phe Tyr Asp Cys Asp Trp Asp Val Ser Tyr Pro Gly
    370                 375                 380

Tyr Asp Ser His Leu Trp Asp Leu Leu Cys Thr Asn Asn Pro Tyr Asn
385                 390                 395                 400

Cys Glu Trp Asp Ser Ser His Glu Lys Tyr Asp Trp Glu Leu Trp Asp
                405                 410                 415

Lys Trp Cys Lys Asp Pro Tyr Asn Cys Asp Trp Asp Ser Ser His Glu
            420                 425                 430

Lys Tyr Asp Trp Asp Leu Trp Asn Lys Trp Cys Lys Asp Pro Tyr Asn
        435                 440                 445

Cys Glu Trp Asp Ser Ser His Glu Lys Tyr Asp Trp Glu Leu Trp Asp
    450                 455                 460

Lys Trp Cys Lys Asp Pro Tyr Asn Cys Asp Trp Asp Ser Ser His Glu
465                 470                 475                 480

Lys Tyr Asp Trp Asp Leu Trp Asn Lys Trp Cys Lys Asp Pro Tyr Asn
                485                 490                 495

Cys Glu Trp Asp Ser Ser His Glu Lys Tyr Asp Trp Glu Leu Trp Asp
            500                 505                 510

Lys Trp Cys Lys Asp Pro Tyr Asn Cys Glu Trp Asp Ser Ser His Glu
        515                 520                 525

Lys Tyr Asp Trp Lys Leu Trp Asp Lys Trp Cys Lys Asp Phe Tyr Asn
    530                 535                 540

Cys Glu Trp Asp Ser Ser His Glu Lys Tyr Asp Trp Glu Leu Trp Asp
545                 550                 555                 560

Lys Trp Cys Lys Asp Ser Tyr Asn Cys Asp Trp Asp Lys Phe His Glu
                565                 570                 575

Lys Tyr Asp Trp Glu Leu Trp Asp Lys Trp Cys Lys Asp Ser Tyr Asn
            580                 585                 590

Cys Asp Trp Asp Lys Phe His Glu Lys Tyr Asp Trp Asp Leu Trp Asn
        595                 600                 605

Lys Trp Cys Lys Asp Ser Tyr Asn Cys Asp Trp Asp Lys Phe His Glu
    610                 615                 620

Lys Tyr Asp Trp Glu Leu Trp Asp Lys Trp Cys Lys Asp Ser Tyr Asn
625                 630                 635                 640

Cys Asp Trp Asp Lys Phe His Glu Lys Tyr Asp Trp Glu Leu Trp Asp
                645                 650                 655
```

-continued

```
Lys Trp Cys Lys Asp Phe Tyr Asn Cys Glu Trp Asp Ser Ser His Glu
            660                 665                 670

Lys Tyr Asp Trp Glu Leu Trp Asp Lys Trp Cys Lys Asp Pro Tyr Asn
        675                 680                 685

Cys Glu Trp Asp Ser Ser His Glu Lys Tyr Asp Trp Glu Leu Trp Asp
    690                 695                 700

Lys Trp Cys Lys Asp Phe Tyr Asn Cys Asp Trp Asp Lys Phe His Glu
705                 710                 715                 720

Lys Tyr Asp Trp Val Leu Trp Asn Lys Trp Cys Lys Asp Pro Tyr Asn
                725                 730                 735

Cys Glu Trp Asp Ser Ser His Glu Lys Tyr Asp Trp Glu Leu Trp Asp
            740                 745                 750

Lys Trp Cys Lys Asp Pro Tyr Asn Cys Asp Trp Asp Lys Phe His Glu
        755                 760                 765

Lys Tyr Asp Trp Asp Leu Trp Asn Lys Trp Cys Lys Asp Pro Tyr Asn
    770                 775                 780

Cys Glu Trp Asp Ser Ser His Glu Lys Tyr Asp Trp Glu Leu Trp Asp
785                 790                 795                 800

Lys Trp Cys Lys Asp Pro Tyr Asn Cys Glu Trp Asp Ser Ser His Glu
                805                 810                 815

Lys Tyr Asp Trp Lys Leu Trp Asp Lys Trp Cys Lys Asp Phe Tyr Asn
            820                 825                 830

Cys Glu Trp Asp Ser Ser His Glu Lys Tyr Asp Trp Glu Leu Trp Asp
        835                 840                 845

Lys Trp Cys Lys Asp Pro Tyr Asn Cys Glu Trp Asp Ser Ser His Glu
    850                 855                 860

Lys Tyr Asp Trp Glu Leu Trp Asp Lys Trp Cys Lys Asp Pro Tyr Asn
865                 870                 875                 880

Cys Glu Trp Asp Ser Ser His Glu Lys Tyr Asp Trp Glu Leu Trp Asn
                885                 890                 895

Lys Trp Cys Lys Asp Pro Tyr Asn Cys Glu Trp Asp Ser Ser His Glu
            900                 905                 910

Lys Tyr Asp Trp Glu Leu Trp Asp Lys Trp Cys Lys Asp Phe Tyr Asn
        915                 920                 925

Cys Glu Trp Asp Ser Ser His Glu Lys Tyr Asp Trp Glu Leu Trp Asp
    930                 935                 940

Lys Trp Cys Lys Asp Pro Tyr Asn Cys Glu Trp Asp Ser Ser His Glu
945                 950                 955                 960

Lys Tyr Asp Trp Glu Leu Trp Asp Lys Trp Cys Lys Asp Phe Tyr Asn
                965                 970                 975

Cys Glu Trp Asp Ser Ser His Glu Lys Tyr Asp Trp Lys Leu Trp Asn
            980                 985                 990

Lys Trp Cys Lys Asp Phe Tyr Asn  Cys Glu Trp Asp Ser  Ser His Glu
        995                 1000                 1005

Lys Tyr  Asp Trp Lys Leu Trp  Asn Lys Trp Cys Lys  Asp Phe Tyr
    1010                 1015                 1020

Asn Cys  Glu Trp Asp Ser Ser  His Glu Lys Tyr Asp  Trp Glu Leu
    1025                 1030                 1035
```

-continued

```
Trp Asn  Lys Trp Cys Asn Lys  His Asp Glu His Asp  Lys His His
    1040                1045                1050

His His  His His
    1055


<210> SEQ ID NO 5
<211> LENGTH: 114
<212> TYPE: PRT
<213> ORGANISM: TR4

<400> SEQUENCE: 5

Met Arg Gly Ser His His His His His His Gly Ile Arg Arg Arg Pro
1               5                   10                  15

Tyr Asn Cys Asp Trp Asp Lys Ser His Glu Lys Tyr Asp Trp Glu Leu
            20                  25                  30

Trp Asp Lys Trp Cys Lys Asp Pro Tyr Asn Cys Asp Trp Asp Lys Ser
        35                  40                  45

His Glu Lys Tyr Asp Trp Glu Leu Trp Asp Lys Trp Cys Lys Asp Pro
    50                  55                  60

Tyr Asn Cys Asp Trp Asp Lys Ser His Glu Lys Tyr Asp Trp Glu Leu
65                  70                  75                  80

Trp Asp Lys Trp Cys Lys Asp Pro Tyr Asn Cys Asp Trp Asp Lys Ser
                85                  90                  95

His Glu Lys Tyr Asp Trp Glu Leu Trp Asp Lys Trp Cys Lys Asp Glu
            100                 105                 110

Leu Ala
```